United States Patent
McBride et al.

(10) Patent No.: US 7,794,938 B2
(45) Date of Patent: Sep. 14, 2010

(54) MULTIPLEX DETECTION OF AGRICULTURAL PATHOGENS

(75) Inventors: Mary Teresa McBride, Brentwood, CA (US); Thomas Richard Slezak, Livermore, CA (US); Sharon Lee Messenger, Kensington, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 642 days.

(21) Appl. No.: 11/652,841

(22) Filed: Jan. 12, 2007

(65) Prior Publication Data

US 2008/0248459 A1    Oct. 9, 2008

(51) Int. Cl.
C07H 21/04    (2006.01)
C12Q 1/68    (2006.01)

(52) U.S. Cl. .......................... 435/6; 435/975; 536/23.1
(58) Field of Classification Search ....................... None
See application file for complete search history.

(56) References Cited

OTHER PUBLICATIONS

Alegre M et al "Development of a multiplex polymerase chain reaction for the differentiation of bovine herpesvirus-1 and -5", Journal of Veterinary Medicine Series B, vol. 48, No. 8, Oct. 2001 pp. 613-621, XP002515954 ISSN: 0931-1793 p. 615.
Deka D et al: "Detection of bovine herpesvirus-1 infection in breeding bull semen by virus isolation and polymerase chain reaction" Revue Scientifique Et Technique-Office International Despizooties/Scientific and Technical Review—International Offfice of Epizootics, Office International Des Epizooties, Paris, FR, vol. 24, No. 3, Dec. 1, 2005, pp. 1085-1094, XP008102208 ISSN: 0253-1933 p. 1087.
El-Kholy Alaa A: "Molecular and immunological detection of bovine herpesvirus-1 in clinical specimens" Egyptian Journal of Immunology, The, Egypt, vol. 12, No. 2, Jan. 1, 2005, pp. 125-136, XP008102410 ISSN: 1110-4902 p. 128.
Harris, C., "Liquid array single-handedly detects bounty of BW agents," Analytical Chemistry, May 1, 2003, p. 202.
Heller, A., "Protecting the Nation's Livestock," S&TR, May 2006, p. 11-17.
McBride, M., et al., "Autonomous Detection of Aerosolized Bacillus anthracis and Yersinia petsis," Analytical Chemistry, Oct. 15, 2003, p. 5293-5299, vol. 75, No. 20.
McBride, M., et al., "Multiplexed Liquid Arrays for Simultaneous Detection of Simulants of Biological Warfare Agents," Analytical Chemistry, Apr. 15, 2003, p. 1924-1930, vol. 75, No. 8.
McBride, M., et al., "Tailored assays for the detection of foreign disease pathogens in animals," IVD Technology, May 2005, p. 49-52, vol. 11, No. 4.
Wilson, W., et al., "A multiplexed PCR-coupled liquid bead array for the simultaneous detection of four biothreat agents," Molecular and Cellular Probes, 2005, p. 137-144, vol. 19.

Callahan, J.D. et al., "Use of a Portable Real-time Reverse Transcriptase-polymerase Chain Reaction Assay for Rapid Detection of Foot-and-Mouth Disease Virus," Journal of the American Veterinary Medical Association, Jun. 1, 2002, vol. 220, No. 11, pp. 1636-1642, 7 pages.
Database EMBL [Online] Sep. 6, 2005, "Bovine Herpesvirus Type 1.1 Isolate T3 Glycoprotein C (gC) Gene, Partial Cds.," XP002515958, Retrieved from EBI Accession No. EMBL:DQ173736, Database Accession No. DQ173736 abstract, 2 pages.
Database EMBL [Online] Apr. 8, 1996, "Sequence 2 from Patent US 5462734," XP002515959, Retrieved from EBI Accession No. EMBL:I15275, Database Accession No. I15275 abstract and US 5,462,734 A (Letchworth III, Geoffrey J. [US] et al.) Oct. 31, 1995, 1 page.
Deregt D. et al., "A Multiplex DNA Suspension Microarray for Simultaneous Detection and Differentiation of Classical Swine Fever Virus and Other Pestiviruses," Journal of Virological Methods, Elsevier BV, NL, Sep. 1, 2006, vol. 136, No. 1-2, pp. 17-23, 7 pages.
Hullinger, P. ,"Agricultural Security Domestic Deomonstration and Application Program (AgDDAP)," NIAA Annual Meeting Proceedings, [Online] 2006, Retrieved from the internet on Jul. 31, 2009: <http://animalagriculture.org/Proceedings/2006/Wednesday/AHEM/6%20Pam%20Hullinger%20speaker%20for%20AHEM.pdf>, 22 pages.
Mahlum, C. et al., "Detection of Bovine Viral Diarrhea Virus by TaqMan Reverse Transcription Polymerase Chain Reaction," Journal of Veternary Diagnostic Investigation: Official Publication of the American Association of Veterinary Laboratory Diagnosticians, Inc., Mar. 2002, vol. 14, No. 2, pp. 120-125, 6 pages.
Reid, S.M. et al., "Detection of All Seven Serotypes of Foot-and-Mouth Disease Virus by Real-time, Fluorogenic Reverse Transcription Polymerase Chain Reaction Assay," Journal of Virological Methods, Elsevier BV, NL, Aug. 1, 2002, vol. 105, No. 1, pp. 67-80, 14 pages.
PCT Invitation to Pay Additional Fees And, Where Applicable, Protest Fee, PCT Application No. PCT/US2008/050304, Apr. 3, 2009, 11 pages.
PCT International Preliminary Report on Patentability, PCT Application No. PCT/US2008/050304, Jul. 14, 2009, 11 pages.
PCT International Search Report and Written Opinion, PCT Application No. US2008/050304, May 14, 2009, 23 pages.

*Primary Examiner*—Mark Navarro
(74) *Attorney, Agent, or Firm*—John H. Lee

(57) ABSTRACT

Described are kits and methods useful for detection of seven agricultural pathogens (BPSV; BHV; BVD; FMDV; BTV; SVD; and VESV) in a sample. Genomic sequence information from 7 agricultural pathogens was analyzed to identify signature sequences, e.g., polynucleotide sequences useful for confirming the presence or absence of a pathogen in a sample. Primer and probe sets were designed and optimized for use in a PCR based, multiplexed Luminex assay to successfully identify the presence or absence of pathogens in a sample.

17 Claims, 6 Drawing Sheets

FIG. 5A

SEQUENCE LISTING

<160> NUMBER OF SEQ ID NOS: 125

<210> SEQ ID NO 1
<211> LENGTH: 140
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 1
gtgccagccg cgtaaaagcg gcgctccatg ttagcgctct ggaaccagga gacgtcgcag    60
cgcaggttgg gcgggtgggc ggttggcgtc gcgtcctcga gcgtaaggac ggacgtgcgc   120
gaaaagagcc cggagtcgtc                                               140

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgccagccg cgtaaaag                                                  18

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gacgactccg ggctctttt                                                 19

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcctggttcc agagcgctaa catggag                                        27

<210> SEQ ID NO 5
<211> LENGTH: 114
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtccccacgg gcgtagtagc accgggcgtg ctgtcctctg gcgtagcgtc ggggctgttg    60
ggcgtggggg gcgttgcgcc ggtggtccca gcggagcttt ccgtctcggt tggg         114

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgaggcctat gtatgggcag tt                                             22
```

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcgcgccaaa cataagtaaa                                                   20

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaataacacg gtgtgcactt aaataagatt cgcg                                   34

<210> SEQ ID NO 9
<211> LENGTH: 178
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcagatgcgc tcctggttct ggcagaacac cgagtcttcg atgatcaaca ccctcctggt       60
cccggccgac cgcatgatgg ccatggcccg gatgagcctc ttcttcgatc cgcgtatgga      120
catggaccgg agcacgttct ccacgtcgga gtcggagacg ttgcagcagc agaggtgc        178

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcagatgcgc tcctggtt                                                     18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcacctctgc tgctgcaa                                                     18

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
```

-continued ccgactccga cgtggagaac gtg                                         23

<210> SEQ ID NO 13
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gatggccgtg cagctcttgg ccgaggcgta cgagaagagc gcgctgttgc ggaagcccat    60
gagcccgtac acggagttgg ccgtgatctt gtacg                              95

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gatggccgtg cagctctt                                               18

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cgtacaagat cacggccaac t                                           21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgtacgggct catgggcttc cg                                          22

<210> SEQ ID NO 17
<211> LENGTH: 167
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcagcagtgc accacgtagt acccggcggt ggcgcgcagg cgcttgttgt ccgcctcgaa    60
gtccgcctcc aacccctcgt tgaagtactt gtcgaatatg atgggcagga aggatagttt   120
tgactcggtg accaccttcc cgaagttgag gatgtacggg ttcagcg                167

<210> SEQ ID NO 18
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 18
gcagcagtgc accacgtagt                                               20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgctgaaccc gtacatcct                                                19

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gacttcgagg cggacaacaa gcg                                           23

<210> SEQ ID NO 21
<211> LENGTH: 107
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
actgggtttt acaaacctgt gatggcctcg aagaccctcg aggccatcct ctcctttgca   60
cgccgtggga ccatacagga gaagttgatc tccgtggcag gactcgc                107

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
actgggtttt acaaacctgt ga                                            22

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgagtcctg ccacgga                                                  17

<210> SEQ ID NO 24
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 24
gtcccacggc gtgcaaagga                                                      20

<210> SEQ ID NO 25
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cactttaaag tgacactgaa actggtaccc aatcactggt gacaggctaa ggatgccctc          60
caggtacccc gaggtaacac gagacactcg ggatctg                                   97

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cacytyaagr tgacaytgrt actggtac                                             28

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: Inosine
<220> FEATURE:
<221> NAME/KEY: modified_base
<222> LOCATION: (18)..(18)
<223> OTHER INFORMATION: Inosine

<400> SEQUENCE: 27
cagatyccra gtgwcncntg tta                                                  23

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cctcggggta cctgaagggc atcc                                                 24

<210> SEQ ID NO 29
<211> LENGTH: 202
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 29
ggtagtcgtc agtggttcga cacctcggaa agaaggtctc gagatgccac gtggacgagg    60
gcatgcccaa agcacatctt aacctggacg ggggtcgccc aggtaaaagc agttttgacc   120
aactgttatg gacacagcct gatagggtgc tgcagaggcc cactgaattg ctactaaaaa   180
tctctgctgt acatggcaca tg                                           202

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggtagtcgtc agtggttcga c                                             21

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
catgtgccat gtacagcaga gat                                           23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cctcgtccac gtggcatctc gag                                           23

<210> SEQ ID NO 33
<211> LENGTH: 255
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcaagacgaa tgaatgagga gaagatctta gaggcggtga agtattcgca aaatttaggc    60
tcgcacgatc gtaggctacc tcttttttgaa aaaatgttaa agatggttta tactacacca   120
ttctacccgc ataagagctc gaacatgata ttagcatctt tcctattaag cattcaaacc   180
attactggat atggcagggc gtgggtgaag aacgtgagca ccgagttcga taaacagctg   240
aaaccgaacc caagc                                                   255

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcaccctata tgtttccaga cca                                          23

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cagctaactc ttcagccaca cg                                           22

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctaactcgtg ggccaatcat catcttctgt                                   30

<210> SEQ ID NO 37
<211> LENGTH: 253
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggatttgcga tatgaaggtt atacgttaga acagatcata gattttggat atggagaggg    60
gagggtagcg aatacgttgt ggaacggaaa gcgaagactg tttaagacta catttgacgc   120
gtatatacga ttagatgaga gcgagcgaga caaaggtggt ttcaaggtcc ccaagggagt   180
gcttccagta tcgagtgttg acgttgcgaa tcgaatcgcg gtggacaagg gattcgacac   240
gcttatcgcg gca                                                     253

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcaccctata tgtttccaga cca                                          23

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cagctaactc ttcagccaca cg                                           22

<210> SEQ ID NO 40

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctaactcgtg ggccaatcat catcttctgt                                       30

<210> SEQ ID NO 41
<211> LENGTH: 299
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
caggataatt tcttccaagg gcccccagga gaggtgatgg gaagagccat ttccagccct      60
aaccgccgca gagacagggc acacgtcaca agttgtacca tcagacacaa tgcaaactag    120
acacgtgaag aattaccatt caagatcaga gtcgacagtg gagaacttcc tgtgcagatc    180
tgcatgcgtc ttctacacca catacaagaa ccatgactcc gatggcgaca acttcgccta    240
ctgggtgatc aacacacggc aagttgctca actgcgtcgg aagctcgaaa tgttcacgt    299

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
caggataatt tcttccaagg gc                                               22

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
acgtgaacat ttcgagcttc c                                                21

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgcattgtgt ctgatggtac aacttgtgac g                                     31

<210> SEQ ID NO 45
<211> LENGTH: 281
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 45
gacttgttgt ggctggagga cgacgccatg gagcaaggag ttagggatta tgtggaacaa     60
ctcggcaact gcttcggctc aggattcacc aatcaaattt gcgaacaggt tacccttcta    120
aaagagtcgt taattggaca ggattctatc cttgagaagt ctctcaaggc cctcgtcaag    180
atagtatcag cactcgtgat cgtggtgaga atcacgatg acctcattac ggtcaccgcc     240
acactggcgt taataggatg cactacctca ccatggcgct g                        281

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gacttgttgt ggctggagga                                                 20

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cagcgccatg gtgaggtag                                                  19

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tgaccgtaat gaggtcatcg tgatttctca c                                    31

<210> SEQ ID NO 49
<211> LENGTH: 248
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gacaaagtgg ccaagggaaa gtccaggctc atcgaggctt ctagcctcaa cgactcagta     60
gcaatgaggc agacatttgg aaacctatat aagactttcc acctcaaccc gggcatcgtt    120
acgggtagcg ccgttgggtg tgacccagat gtcttttgga gcaagattcc cgtcatgctc    180
gatggacatc tcatagcgtt tgactattca ggctatgacg ccagcctcag cccagtgtgg    240
tttacgtg                                                             248

<210> SEQ ID NO 50
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 50
gacaaagtgg ccaagggaaa                                                   20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cacgtaaacc acactgggct                                                   20

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctggcgtcat agcctgaata gtcaaacgct a                                      31

<210> SEQ ID NO 53
<211> LENGTH: 153
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gccttctccc ttcccaaaac ggacggaccc accggaaacg aacccgaatt catcgctgag       60
gcttgcccta gctgcgctct ttacgacacg tgtccaaatt gcacatctaa ggttatcaac      120
gatgatggct caactgacgg aaccattcct tca                                   153

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gccttctccc ttcccaaaa                                                    19

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tgaaggaatg gttccgtcag t                                                 21

<210> SEQ ID NO 56
<211> LENGTH: 34

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
catcatcgtt gataacctta gatgtgcaat ttgg                          34

<210> SEQ ID NO 57
<211> LENGTH: 199
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
gggaatgagg tgtgcatcat tgatgaattc gactcatctg acaaggttga ttatgccaat    60
tttgtagtca acatggttaa caccaacccc atggtcttaa attgtgatct aattgaaaac   120
aaaggcaaga cattcacctc aaaatacgtc atcatgacgt ccaacacgga aacaccagtc   180
aagccaacat caagacgtg                                               199

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
gggaatgagg tgtgcatcat t                                        21

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
cacgtcttga tgttggcttg ac                                       22

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
aaattggcat aatcaacctt gtcagatgag tcg                           33

<210> SEQ ID NO 61
<211> LENGTH: 124
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61

```
ggtcgctctc actgatgatg agtacaatga ttggaaacag tccaaagctg aaaaaaacct    60
cgacctcacg gtcaaggact tcctccaact caggcaccga gctgcaatgg gtgctgataa   120
cacc                                                                124
```

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
ggtcgctctc actgatgatg agta                                           24
```

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
ggtgttatca gcacccattg c                                              21
```

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
gctcggtgcc tgagttggag gaag                                           24
```

<210> SEQ ID NO 65
<211> LENGTH: 200
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

```
accacctctg gaaacatcta tggagcctgc ggctcatcgt gttcactgac gagacagggt    60
gactgcggtc tcccctacgt cgacgatcac ggtgttgtcg ttggactcca tgctgggtct   120
ggtggtgaca aatgcccgtc ccgaaaactc attgttccct acgtcaaggt ggatatgaga   180
attcgtgaca cgtgcacaaa                                               200
```

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66

```
accacctctg gaaacatcta tgg                                            23
```

<210> SEQ ID NO 67

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tttgtgcacg tgtcacgaat                                                 20

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cgggacgggc atttgtcacc a                                               21

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ctccatgtta gcgctctgga acctgga                                         27

<210> SEQ ID NO 70
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cgcgaatctt atttaagtgc acaccgtgtt attt                                 34

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cacgttctcc acgtcggagt cgg                                             23

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cggaagccca tgagcccgta ca                                              22

<210> SEQ ID NO 73
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cgcttgttgt ccgcctcgaa gtc                                              23

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
acagaagatg atgattggcc cacgagttag                                       30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctaactcgtg ggccaatcat catcttctgt                                       30

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ctcgagatgc cacgtggacg agg                                              23

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
cctcggggta cctgaagggc atcc                                             24

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gtcccacggc gtgcaaagga                                                  20

<210> SEQ ID NO 79
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 79
cgtcacaagt tgtaccatca gacacaatgc a                                   31

<210> SEQ ID NO 80
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tgaccgtaat gaggtcatcg tgatttctca c                                   31

<210> SEQ ID NO 81
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ctggcgtcat agcctgaata gtcaaacgct a                                   31

<210> SEQ ID NO 82
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ccaaattgca catctaaggt tatcaacgat gatg                                34

<210> SEQ ID NO 83
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cgactcatct gacaaggttg attatgccaa ttt                                 33

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cttcctccaa ctcaggcacc gagc                                           24

<210> SEQ ID NO 85
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 85
tggtgacaaa tgcccgtccc g                                                    21

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: iBiodT
<220> FEATURE:
<221> NAME/KEY: modified_base
<222> LOCATION: (21)..(21)
<223> OTHER INFORMATION: iBiodT

<400> SEQUENCE: 86
tgaggccnat gtatgggcag nt                                                   22

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iBiodT
<220> FEATURE:
<221> NAME/KEY: modified_base
<222> LOCATION: (14)..(14)
<223> OTHER INFORMATION: iBiodT

<400> SEQUENCE: 87
gcagangcgc tccnggtt                                                        18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: iBiodT
<220> FEATURE:
<221> NAME/KEY: modified_base
<222> LOCATION: (15)..(15)
<223> OTHER INFORMATION: iBiodT

<400> SEQUENCE: 88
gatggccgng cagcnctt                                                        18

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (8)..(8)
<223> OTHER INFORMATION: iBiodT
<220> FEATURE:
<221> NAME/KEY: modified_base
<222> LOCATION: (17)..(17)
<223> OTHER INFORMATION: iBiodT

<400> SEQUENCE: 89
gcagcagngc accacgnagt                                               20

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: iBiodT
<220> FEATURE:
<221> NAME/KEY: modified_base
<222> LOCATION: (15)..(15)
<223> OTHER INFORMATION: iBiodT

<400> SEQUENCE: 90
gcacccnata tgttnccaga cca                                           23

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iBiodT
<220> FEATURE:
<221> NAME/KEY: modified_base
<222> LOCATION: (12)..(12)
<223> OTHER INFORMATION: iBiodT

<400> SEQUENCE: 91
agaatncagg angggcagga                                               20

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: iBiodT
<220> FEATURE:
<221> NAME/KEY: modified_base
<222> LOCATION: (17)..(17)
<223> OTHER INFORMATION: iBiodT

<400> SEQUENCE: 92
ggtagtcgnc agtggtncga c                                             21

<210> SEQ ID NO 93
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: iBiodT
<220> FEATURE:
<221> NAME/KEY: modified_base
<222> LOCATION: (23)..(23)
<223> OTHER INFORMATION: iBiodT

<400> SEQUENCE: 93
cacytyaagr ngacaytgrt acnggtac                                              28

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: iBiodT
<220> FEATURE:
<221> NAME/KEY: modified_base
<222> LOCATION: (18)..(18)
<223> OTHER INFORMATION: iBiodT

<400> SEQUENCE: 94
actgggnttt acaaaccngt ga                                                    22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iBiodT
<220> FEATURE:
<221> NAME/KEY: modified_base
<222> LOCATION: (14)..(14)
<223> OTHER INFORMATION: iBiodT

<400> SEQUENCE: 95
cagganaatt tctnccaagg gc                                                    22

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: iBiodT
<220> FEATURE:
<221> NAME/KEY: modified_base
<222> LOCATION: (14)..(14)
<223> OTHER INFORMATION: iBiodT

<400> SEQUENCE: 96
```
gacttgntgt ggcnggagga                                              20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: iBiodT

<400> SEQUENCE: 97
gacaaagngg ccaagggaaa                                              20

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: iBiodT
<220> FEATURE:
<221> NAME/KEY: modified_base
<222> LOCATION: (12)..(12)
<223> OTHER INFORMATION: iBiodT

<400> SEQUENCE: 98
gcctnctccc tncccaaaa                                               19

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iBiodT
<220> FEATURE:
<221> NAME/KEY: modified_base
<222> LOCATION: (17)..(17)
<223> OTHER INFORMATION: iBiodT

<400> SEQUENCE: 99
gggaangagg tgtgcancat t                                            21

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: iBiodT
<220> FEATURE:
<221> NAME/KEY: modified_base
<222> LOCATION: (19)..(19)
<223> OTHER INFORMATION: iBiodT

<400> SEQUENCE: 100
ggtcgcnctc actgatgang agta                                    24

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: iBiodT
<220> FEATURE:
<221> NAME/KEY: modified_base
<222> LOCATION: (19)..(19)
<223> OTHER INFORMATION: iBiodT

<400> SEQUENCE: 101
accaccnctg gaaacatcna tgg                                     23

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
caaagtggga gacgtcgttg                                         20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: iBiodT
<220> FEATURE:
<221> NAME/KEY: modified_base
<222> LOCATION: (18)..(18)
<223> OTHER INFORMATION: iBiodT

<400> SEQUENCE: 103
caaagnggga gacgtcgntg                                         20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
caaagtggga gacgtcgttg                                         20

<210> SEQ ID NO 105
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gacatcaagg ctcaaactaa ttttacc                                        27

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
caaaggctgc aacataaaa tg                                              22

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
caagcgtaaa tgcagcgtcc a                                              21

<210> SEQ ID NO 108
<211> LENGTH: 131
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (81)..(98)
<223> OTHER INFORMATION: a, c, g, t, unknown or other

<400> SEQUENCE: 108
caaacctgtg atggcttcga agaccctcga agctatcctc tcctttgcac gccgtgggac    60
cattcaggag aagttgatct nnnnnnnnnn nnnnnnnntc cactccggac aagacgagta   120
ccggcgtctc t                                                       131

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
caaacctgtg atggcttcga                                                20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
agagacgccg gtactcgtct t                                              21

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tgcacgccgt gggaccattc                                              20

<210> SEQ ID NO 112
<211> LENGTH: 131
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(51)
<223> OTHER INFORMATION: a, c, g, t, unknown or other

<400> SEQUENCE: 112
agagacgccg gtactcgtct tgtccggagt ggannnnnnn nnnnnnnnnn nagatcaact      60
tctcctgaat ggtcccacgg cgtgcaaagg agaggatagc ttcgagggtc ttcgaagcca    120
tcacaggttt g                                                        131

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
agagacgccg gtactcgtct t                                             21

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
caaacctgtg atggcttcga                                               20

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tcctgaatgg tcccacggcg t                                             21

<210> SEQ ID NO 116
<211> LENGTH: 166
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: modified_base
<222> LOCATION: (45)..(62)
<223> OTHER INFORMATION: a, c, g, t, unknown or other
<220> FEATURE:
<221> NAME/KEY: modified_base
<222> LOCATION: (93)..(110)
<223> OTHER INFORMATION: a, c, g, t, unknown or other

<400> SEQUENCE: 116
ccaacgcagg taaagtgatc tgtagcttgg aatctcgaac gtccnnnnnn nnnnnnnnnn      60
nngacgccgg tactcgtctt gtccggagtg gannnnnnnn nnnnnnnnnn agatcaactt     120
ctcctgaatg gtcccacggc gtgcaaagga gaggatagct tcgagg                   166

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ccaacgcagg taaagtgatc tg                                              22

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
aacctgtgat ggcttcgaag ac                                              22

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tcctgaatgg tcccacggcg t                                               21

<210> SEQ ID NO 120
<211> LENGTH: 343
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (135)..(220)
<223> OTHER INFORMATION: a, c, g, t, unknown or other

<400> SEQUENCE: 120
agcatcatca acacaattct gaacaacatc tacgtgctct acgcgctgcg taggcactac      60
gagggagttg agctggacac ttacaccatg atctcctacg gggacgacat cgtggttgca     120
agtgattacg atctnnnnnn nnnnnnnnnn nnnnnnnnnn nnnnnnnnnn nnnnnnnnnn     180
nnnnnnnnnn nnnnnnnnnn nnnnnnnnnn nnnnnnnnnn gtcactccat taccgatgtc     240
```

```
actttcctca aaagacactt ccacatggat tatggaactg ggttttacaa acctgtgatg      300
gcttcgaaga ccctcgaagc catcctctcc tttgcacgcc gtg                       343
```

<210> SEQ ID NO 121
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121

```
agcatcatca acacaattct gaaca                                            25
```

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122

```
catcacaggt ttgtaaaacc cagtt                                            25
```

<210> SEQ ID NO 123
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123

```
cactttcctc aaaagacact tccacatgga ttatg                                 35
```

<210> SEQ ID NO 124
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124

```
atccgcgcat ag                                                          12
```

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: iBiodT
<220> FEATURE:
<221> NAME/KEY: modified_base
<222> LOCATION: (13)..(13)
<223> OTHER INFORMATION: iBiodT

<400> SEQUENCE: 125

```
gngccagccg cgnaaaag                                                    18
```

MULTIPLEX DETECTION OF AGRICULTURAL PATHOGENS

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

1. Field of the Invention

The invention relates to nucleic acid based kits and methods for determining the presence or absence in a sample of the following seven agricultural pathogens: Foot-and-Mouth Disease virus (FMDV), Bovine Viral Diarrhea (BVD), Bovine Herpes Virus-1 (BHV), Bovine Papular Stomatitis virus (BPSV), Blue Tongue virus (BTV), Swine Vesicular Disease virus (SVD), and Vesicular Exanthema of Swine virus (VESV).

2. Description of the Related Art

Agriculture is a major sector of the U.S. economy, accounting for more than 13% of the gross domestic product, and employing more than 15% of the U.S. population. Cattle and dairy farmers alone earn between $50 billion and $54 billion a year through meat and milk sales, and roughly $50 billion is raised every year through farm-related exports. Overall livestock sales in 2001 were in excess of $108 billion.

An agro-terrorism attack in the U.S. could cause devastating economic consequences, not only for the affected agribusinesses but also for allied industries and services, disrupting food supplies, trade, and tourism. Moreover, because of the structure of American agribusiness (e.g., highly concentrated herds with frequent movement, suboptimal animal tracking systems, minimal farm security/surveillance), agricultural and food industries are quite vulnerable to such an attack.

The agricultural community currently views an introduction of foot-and-mouth disease (FMD) into the United States as one of their greatest concerns. FMD is a severe, highly communicable viral disease of cattle, other ruminants, and swine, FMD is endemic to many countries in the world, and the virus is easy to obtain. Because FMD does not pose a direct threat to human health, there is no need for elaborate containment procedures or personal protective equipment while handling or preparing the virus. Recent estimates associated with the 2001 FMD outbreak in the United Kingdom place economic losses at greater than $30 billion (U.S.).

The Animal and Plant Health Inspection Service (APHIS), a branch of the U.S. Department of Agriculture (USDA), is charged with protecting the nation's livestock and poultry from the introduction of foreign animal diseases and for coordinating the response to an agricultural disease outbreak. The current system for detecting a foreign animal disease (FAD) such as FMD generally involves the following components: (1) observations by veterinary practitioners and livestock owners, who likely will be the first to suspect and report a FAD case; (2) investigation of suspect cases and submission of samples to USDA/APHIS at the Plum Island Animal Disease Center (PIADC); and (3) diagnostic work-up of tissues at the Plum Island Foreign Animal Diagnostic Disease Laboratory (FADDL). Currently, all testing for FMD is done (by law) at FADDL on Plum Island, which averages about 300 investigations per year. During a major outbreak, demand could rise to 100 investigations per week. The number of required diagnostic tests would far exceed current analysis capacity, and authorities would have to resort to subjective clinical observations to determine if herds must be destroyed.

A critical problem facing the USDA/APHIS and state agriculture departments in combating an outbreak of FMD is the lack of rapid, validated diagnostic assays for detection and identification of FMD. The need for improved diagnostics and surveillance programs to better enable the United Sates to detect and respond to foreign animal diseases (FADs) has been highlighted in several reports (e.g. National Association of State Departments of Agriculture and Research Foundation, the General Accounting Office, and the National Research Council) as well as Homeland Security Presidential Directive-9 (HSPD-9). Additionally, recent outbreaks of FMD in South America and the United Kingdom have heightened concerns about the ability of existing US surveillance systems to rapidly detect a FMD incursion early in the course of an outbreak and then provide the required diagnostic surge capacity needed for an outbreak response and the recovery of disease free status.

At PIADC, laboratory methods currently used to detect FADs include agar gel immunodiffusion assays, enzyme-linked immunosorbent assays (ELISA), serum neutralization assays, virus isolation in tissue culture, direct fluorescent antibody tests, electron microscopy, and animal inoculation. These methods are generally time-consuming and labor-intensive. Rapid polymerase chain reaction (PCR) assays have been used on a limited basis and a few rapid diagnostic tests are currently undergoing validation, but these tests are not yet available. (Callahan, J. D.; Brown, F.; Csorio, F. A.; Sur, J. H.; Kramer, E.; Long, G. W.; Lubroth, J.; Ellis. S. J.; Shoulars, K. S.; Gaffney, K. L.; Rock, D. L.; Nelson, W. M. "Use of a portable real-time reverse transcriptase-polymerase chain reaction assay for rapid detection of foot-and-mouth disease virus." J. Am. Vet. Med. Assn., 220 (11) 1636-1642, Jun. 1, 2002.)

APHIS also lacks rapid, validated diagnostic assays that can differentiate FMD from the many "look-alike" diseases indigenous to the animal agricultural industries (e.g., bovine viral diarrhea virus, contagious ecthyma, bluetongue virus). These domestic diseases induce signs that are similar to FMD: drooling, blisters, or lameness. In the absence of an FMD outbreak, these look-alike diseases can instill a sense of complacency on the part of practitioners and producers, who may have seen similar signs before and thus, believe these signs are the result of common enzootic diseases. When a practitioner notifies a regulatory agency of a suspicious disease, animal samples are sent to PIADC for FAD diagnosis only, not for diagnosis of look-alike domestic diseases. Consequently, without the ability to offer a timely diagnosis for the look-alike diseases that are indigenous, practitioners and producers might disregard important disease signs or develop a disinterest in becoming involved in an FAD investigation of their animals. In an actual FMD outbreak, however, the tendency is to err on the side of over-diagnosis. In the 2001 United Kingdom FMD outbreak, field diagnoses based on clinical observations resulted in a large number of false positive diagnoses (estimates are as high as 70-80%) and unnecessary slaughter of herds (4.3 million animals slaughtered), with only 2023 laboratory-confirmed cases of FMD.

Traditional approaches to DNA signature development started with the hypothesis that a particular gene was vital to the organism's virulence, host range, or other factors that might be considered "unique". Suitable primers and probe were designed for the detection system of choice, with or without computational screening (via BLAST or equivalent) for uniqueness. The resulting assay would then be tested with the available strain(s) and success declared if the targets were detected, but the assay didn't detect whatever near-neighbors were tested. This approach would sometimes yield good results, but failures occurred due to inadequate strain panel coverage and cross reactions with genetic near neighbors and complex environmental samples.

SUMMARY OF THE INVENTION

Disclosed herein is a rapid, multiplexed nucleic acid panel, e.g., a kit for the detection of Foot and Mouth Disease Virus (FMDV) and its differentiation from a number of other viruses that cause clinical signs in animals that are indistinguishable from FMDV. The diagnostic assay panel detects 17 signature sequences, e.g., unique nucleic acid sequences, for 7 agricultural pathogens as follows: Foot and Mouth Disease Virus (FMDV, 2 signatures), Bovine Herpes Virus-1 (BHV-1, 2 signatures), Bovine Papular Stomatitis Virus (BPSV, 3 signatures), Bovine Viral Diarrhea Virus (BVD, 1 signature), Bluetongue Virus (BTV (domestic) 2 signatures), Swine Vesicular Disease Virus (SVD, 3 signatures) and Vesicular Exanthema of Swine Virus (VESV, 4 signatures). The signature sequences are presented in Table 1. The kit includes nucleic acid reagents, e.g., amplification primers and hybridization probes, for detection of the signature sequences; exemplary nucleic acid reagents are listed in Table 1. In some embodiments, the probes for detection of amplified signature sequences, e.g., the amplicons are affixed to fluorescent microbeads for analysis using a Luminex instrument.

Accordingly, one embodiment of the invention are kits for determining the presence or absence of at least one pathogen in a sample selected from the group consisting of BVH, BPSV, FMDV; BVD, BTV; SVD; and VESV. The kits of the invention include nucleic acid reagents for detection of at least one nucleic acid signature sequence from each of the at least one pathogens as listed in Table 1, wherein the following nucleic acid signature sequences are detected: for pathogen BVH, signature sequences consisting of SEQ ID NO:1 or SEQ ID NO:5; for pathogen BPSV, signature sequences consisting of SEQ ID NO:9 or SEQ ID NO:13 or SEQ ID NO:17; for pathogen BVD, signature sequences consisting of SEQ ID NO:29; for pathogen BTV, signature sequences consisting of SEQ ID NO:33 or SEQ ID NO:37; for pathogen SVD, signature sequences consisting of SEQ ID NO:41 or SEQ ID NO:45 or SEQ ID NO:49; and for pathogen VESV, signature sequences consisting of SEQ ID NO:53 or SEQ ID NO:57 or SEQ ID NO:61 or SEQ ID NO:65.

The kits can include reagents for detection of a single agricultural pathogen or of all the recited agricultural pathogens or any combination thereof, e.g., any two, any three, any four, any five, or any six of the recited pathogens. The kits can include reagents for the detection of an individual signature sequence or any combination of signature sequences, or all of the recited signature sequences.

In another embodiment, kits of the invention also include reagents for determining the presence or absence of FMDV in the sample, said kit including nucleic acid reagents for detection of at least one nucleic acid signature sequence selected from the group consisting of SEQ ID NO:21 and SEQ ID NO:25.

In some embodiments, the kits of the invention include a set of oligonucleotides for each signature sequence to be detected, including PCR primers and/or hybridization probes for each signature sequence. Exemplary oligonucleotides are listed in Table 1. The kits can include at least one or all or any combination of the oligonucleotides recited in Table 1. In one embodiment, the kits include all of the oligonucleotides listed in table 1.

The kits of the invention can include reagents for detection of control sequences, e.g., internal controls, negative controls, and the like. Exemplary reagents for detection of control sequences are disclosed in Table 6.

In some embodiments, the kits of the invention include hybridization probes that are affixed to microbeads, e.g., fluorescent microbeads to be analyzed using a Luminex detector.

The invention also includes methods for determining the presence or absence of at least one pathogen selected from the group consisting of BVH, BPSV, BVD, BTV; SVD; and VESV in a sample using the kits described herein. In some embodiments, the methods include PCR amplification of each signature sequence.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 5 illustrates dose response curves for detection of the agricultural pathogens. FIG. 5A: The curves combined herewith represent common viral extraction units (pfu/mL) of representative strains for BHV, BPSV, BTV, BVDV and FMDV.

DETAILED DESCRIPTION OF THE INVENTION

Advantages and Utility

Figure 1:
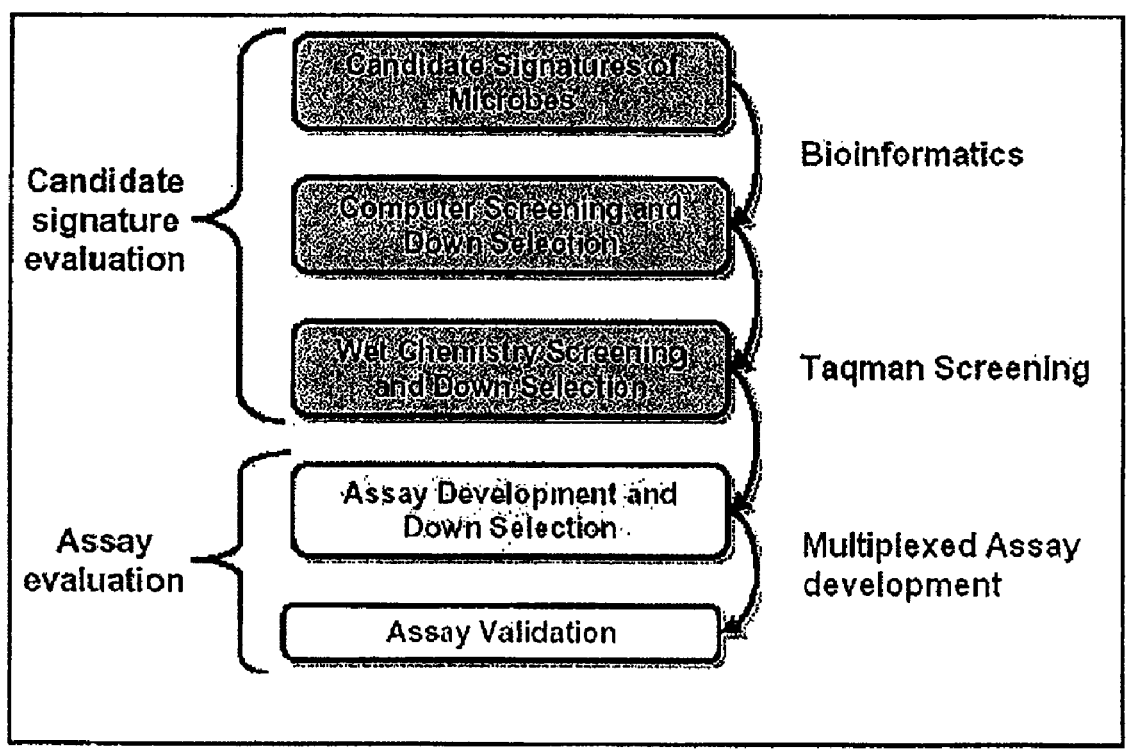
FIG. 1 illustrates the assay development scheme for identification of signature sequences and multiplexed assay development and validation.

Briefly, and as described in more detail below, disclosed and claimed herein are kits and methods for determining the presence or absence of the agricultural pathogens in a sample. The kits and methods utilize nucleic acid based methods for detection of at least one signature nucleic acid sequence corresponding to at least one agricultural pathogen of interest. In one embodiment, the presence or absence of all the agricultural pathogens is determined by detection of all disclosed signature sequences. In one embodiment, the signature sequences are amplified using exemplary primers disclosed herein, and the resulting amplicons are detected using hybridization probes (sequences disclosed herein) affixed to beads in a liquid array format; amplicons hybridized to probes affixed to beads are detected using a Luminex instrument.

Multiplexed detection capabilities provide many advantages over conventional detection methodologies. In the event of an outbreak of an agricultural pathogen, the use of multiplexed assay panels can provide rapid, sensitive, specific and cost-effective means of handling high volumes of samples. The assay panels can greatly improve response time and provide rapid results that can help reduce the impact of infectious disease outbreaks. The use of bead-based liquid arrays has proven to be a well adapted and versatile technology that can be custom tailored to rapidly screen for both DNA and RNA in a single tube, while also allowing for multi-loci detection.

The multiplexed assays are liquid arrays on a commercially available flow cytometer, e.g., a Luminex Bio-Plex. The liquid arrays utilize surface-functionalized polystyrene microbeads, embedded with precise ratios of red and infrared fluorescent dyes. There are 100 unique dye ratios, giving rise to 100 unique bead classes. When excited by a 635-nm laser, the two dyes emit light at different wavelengths, 658 and 712 nm and thus each bead class has a unique spectral address. Bead classes can be easily distinguished and therefore they can be combined and up to 100 different analytes can be measured simultaneously within the same sample. Although the liquid arrays have been demonstrated in a variety of applications, including detection of antigen, antibodies, small molecules, and peptides, in this application, beads are functionalized with a nucleic acid probe of approximately 30 oligonucleotides, where the probe sequence is complimentary to the desired target amplicon. Nucleic acid from the pathogen of interest is extracted, and amplified in an off-line PCR reaction. The PCR reaction is conducted using a mixture of all forward and reverse primers for each of the pathogen targets in the multiplexed panel. The current multiplexed panel comprises 16 different target assays and 4 internal controls, for a total of 17 distinct primer/probe sets. All 34 forward and reverse primers are contained in the PCR reaction mixture and the amplified product is then introduced to the bead mixture (containing all 20 probes), allowed to hybridize, and subsequently labeled with the fluorescent reporter, strepavidin-phycroerythrin. Each optically encoded and fluorescently-labeled microbead is then interrogated by the Luminex flow cytometer. A red laser excites the dye molecules inside the bead and classifies the bead to its unique bead set, and a green laser quantifies the assay at the bead surface. The flow cytometer is capable of reading several thousand beads each second; analysis can be completed in as little as 15 seconds.

The approach disclosed herein is more rapid than prior assays. Results on a clinical sample can be provided in about 4 hours, including sample preparation and processing, and data analysis.

Finally, the approach provides improved strain panel coverage and reduces cross-reactions with genetic near neighbors and complex environmental samples.

Definitions

Terms used in the claims and specification are defined as set forth below unless otherwise specified.

"Signature sequence" refers to a nucleic acid sequence specific and unique to an agricultural pathogen such that it can be used for detection of the pathogen in a sample.

"Amplicon" refers to the amplified product of a nucleic acid amplification reaction, e.g., the product of amplification of a signature sequence.

"Pathogen" means any disease-producing agent (especially a virus or bacterium or other microorganism).

"Agricultural pathogen" means a pathogen capable of infecting animals or plants that are domesticated or propagated through human labor.

"Polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

"Oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

"Percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

It must be noted that, as used in the specification and the appended claims, the singular forms "a," "an" and "the" include plural referents unless the context clearly dictates otherwise.

Kits and Methods of the Invention

Disclosed herein is a rapid, multiplexed nucleic acid panel, e.g., a kit for the detection of seven agricultural pathogens including Foot and Mouth Disease Virus (FMDV) and its differentiation from a number of other viruses that cause clinical signs in animals that are indistinguishable from FMDV. The diagnostic assay panel detects 17 signature sequences, e.g., unique nucleic acid sequences, for 7 agricultural pathogens as follows: Foot and Mouth Disease Virus (FMDV, 2 signatures), Bovine Herpes Virus-1 (BHV-1, 2 signatures), Bovine Papular Stomatitis Virus (BPSV, 3 signatures), Bovine Vial Diarrhea Virus (BVD, 1 signature), Bluetongue Virus (BTV (domestic) 2 signatures), Swine Vesicular Disease Virus (SVD, 3 signatures) and Vesicular Exanthema of Swine Virus (VESV, 4 signatures). The signature sequences are presented in Table 1.

TABLE 1

Signature sequences, PCR primers, and probes for detection of 7 agricultural pathogens in a sample.

| SEQ ID NO: | Pathogen_ Assay | description | Sequence 5' => 3' |
|---|---|---|---|
| 1 | BVH_1 | SIGNATURE SEQUENCE 140 bp | GTGCCAGCCGCGTAAAAGCGGCGCTC<br>CATGTTAGCGCTCTGGAACCAGGAGA<br>CGTCGCAGCGCAGGTTGGGCGGGTGG<br>GCGGTTGGCGTCGCGTCCTCGAGCGT<br>AAGGACGGACGTGCGCGAAAAGAGCC<br>CGGAGTCGTC |
| 2 | BVH_1 | FORWARD PRIMER | GTGCCAGCCGCGTAAAAG |
| 3 | BVH_1 | REVERSE PRIMER | GACGACTCCGGGCTCTTTT |
| 4 | BVH_1 | PROBE | TCCTGGTTCCAGAGCGCTAACATGGA<br>G |
| 5 | BVH_3 | SIGNATURE SEQUENCE 114 bp | GTCCCCACGGGCGTAGTAGCACCGGG<br>CGTGCTGTCCTCTGGCGTAGCGTCGG<br>GGCTGTTGGGCGTGGGGGGCGTTGCG<br>CCGGTGGTCCCAGCGGAGCTTTCCGT<br>CTCGGTTGGG |
| 6 | BVH_3 | FORWARD PRIMER | TGAGGCCTATGTATGGGCAGTT |
| 7 | BVH_3 | REVERSE PRIMER | GCGCGCCAAACATAAGTAAA |
| 8 | BVH_3 | PROBE | AAATAACACGGTGTGCACTTAAATAA<br>GATTCGCG |
| 9 | BPSV-1 | SIGNATURE SEQUENCE 178 bp | GCAGATGCGCTCCTGGTTCTGGCAGA<br>ACACCGAGTCTTCGATGATCAACACC<br>CTCCTGGTCCCGGCCGACCGCATGAT<br>GGCCATGGCCCGGATGAGCCTCTTCT<br>TCGATCCGCGTATGGACATGGACCGG<br>AGCACGTTCTCCACGTCGGAGTCGGA<br>GACGTTGCAGCAGCAGAGGTGC |
| 10 | BPSV-1 | FORWARD PRIMER | GCAGATGCGCTCCTGGTT |
| 11 | BPSV-1 | REVERSE PRIMER | GCACCTCTGCTGCTGCAA |
| 12 | BPSV-1 | PROBE | CCGACTCCGACGTGGAGAACGTG |
| 13 | BPSV_2 | SIGNATURE SEQUENCE 95 bp | GATGGCCGTGCAGCTCTTGGCCGAGG<br>CGTACGAGAAGAGCGCGCTGTTGCGG<br>AAGCCCATGAGCCCGTACACGGAGTT<br>GGCCGTGATCTTGTACG |
| 14 | BPSV_2 | FORWARD PRIMER | GATGGCCGTGCAGCTCTT |
| 15 | BPSV_2 | REVERSE PRIMER | CGTACAAGATCACGGCCAACT |
| 16 | BPSV_2 | PROBE | TGTACGGGCTCATGGGCTTCCG |
| 17 | BPSV_4 | SIGNATURE SEQUENCE 167 bp | GCAGCAGTGCACCACGTAGTACCCGG<br>CGGTGGCGCGCAGGCGCTTGTTGTCC<br>GCCTCGAAGTCCGCCTCCAACCCCTC<br>GTTGAAGTACTTGTCGAATATGATGG<br>GCAGGAAGGATAGTTTTGACTCGGTG<br>ACCACCTTCCCGAAGTTGAGGATGTA<br>CGGGTTCAGCG |
| 18 | BPSV_4 | FORWARD PRIMER | GCAGCAGTGCACCACGTAGT |
| 19 | BPSV_4 | REVERSE PRIMER | CGCTGAACCCGTACATCCT |

TABLE 1-continued

Signature sequences, PCR primers, and probes for detection of 7 agricultural pathogens in a sample.

| SEQ ID NO: | Pathogen_Assay | description | Sequence 5' => 3' |
|---|---|---|---|
| 20 | BPSV_4 | PROBE | GACTTCGAGGCGGACAACAAGCG |
| 21 | FMDV-TC | SIGNATURE SEQUENCE 280 bp | ACTGGGTTTTACAAACCTGTGATGGCCTCGAAGACCCTCGAGGCCATCCTCTCCTTTGCACGCCGTGGGACCATACAGGAGAAGTTGATCTCCGTGGCAGGACTCGC |
| 22 | FMDV-TC | FORWARD PRIMER | ACTGGGTTTTACAAACCTGTGA |
| 23 | FMDV-TC | REVERSE PRIMER | GCGAGTCCTGCCACGGA |
| 24 | FMDV-TC | PROBE | GTCCCACGGCGTGCAAAGGA |
| 25 | FMDV-pir | SIGNATURE SEQUENCE 280 bp | CACTTTAAAGTGACACTGAAACTGGTACCCAATCACTGGTGACAGGCTAAGGATGCCCTCCAGGTACCCCGAGGTAACACGAGACAC -TCGGGATCTG |
| 26 | FMDV-pir | FORWARD PRIMER | CACYTYAAGRTGACAYTGRTACTGGTAC |
| 27 | FMDV-pir | REVERSE PRIMER | CAGATYCCRAGTGWCICITGTTA |
| 28 | FMDV-pir | PROBE | CCTCGGGGTACCTGAAGGGCATCC |
| 29 | BVD_1a | SIGNATURE SEQUENCE 202 bp | GGTAGTCGTCAGTGGTTCGACACCTCGGAAAGAAGGTCTCGAGATGCCACGTGGACGAGGGCATGCCCAAAGCACATCTTAACCTGGACGGGGGTCGCCCAGGTAAAAGCAGTTTTGACCAACTGTTATGGACACAGCCTGATAGGGTGCTGCAGAGGCCCACTGAATTGCTACTAAAAATCTCTGCTGTACATGGCACATG |
| 30 | BVD_1a | FORWARD PRIMER | GGTAGTCGTCAGTGGTTCGAC |
| 31 | BVD_1a | REVERSE PRIMER | CATGTGCCATGTACAGCAGAGAT |
| 32 | BVD_1a | PROBE | CCTCGTCCACGTGGCATCTCGAG |
| 33 | BTV_2 | SIGNATURE SEQUENCE 271 bp | TCAAGACGAATGAATGAGGAGAAGATCTTAGAGGCGGTGAAGTATTCGCAAAATTTAGGCTCGCACGATCGTAGGCTACCTCTTTTTGAAAAAATGTTAAAGATGGTTTATACTACACCATTCTACCCGCATAAGAGCTCGAACATGATATTAGCATCTTTCCTATTAAGCATTCAAACCATTACTGGATATGGCAGGGCGTGGGTGAAGAACGTGAGCACCGAGTTCGATAAACAGCTGAAACCGAACCCAAGC |
| 34 | BTV_2 | FORWARD PRIMER | GCACCCTATATGTTTCCAGACCA |
| 35 | BTV_2 | REVERSE PRIMER | CAGCTAACTCTTCAGCCACACG |
| 36 | BTV_2 | PROBE | CTAACTCGTGGGCCAATCATCATCTTCTGT |
| 37 | BTV_3 | SIGNATURE SEQUENCE 187 bp | GGATTTGCGATATGAAGGTTATACGTTAGAACAGATCATAGATTTTGGATATGGAGAGGGGAGGGTAGCGAATACGTTGTGGAACGGAAAGCGAAGACTGTTTAAGACTACATTTGACGCGTATATACGATTAGATGAGAGCGAGCGAGACAAAGGTGGTTTCAAGGTCCCCAAGGGAGTGCTTCCAGTATCGAGTGTTGACGTTGCGAATCGAATCGCGGTGGACAAGGGATTCGACACGCTTATCGCGGCA |
| 38 | BTV_3 | FORWARD PRIMER | GCACCCTATATGTTTCCAGACCA |
| 39 | BTV_3 | REVERSE PRIMER | CAGCTAACTCTTCAGCCACACG |
| 40 | BTV_3 | PROBE | CTAACTCGTGGGCCAATCATCATCTTCTGT |
| 41 | SVD_1 | SIGNATURE SEQUENCE 349 bp | CAGGATAATTTCTTCCAAGGGCCCCCAGGAGAGGTGATGGGAAGAGCCATTTCCAGCCCTAACCGCCGCAGAGACAGGGCACACGTCACAAGTTGTACCATCAGACACAATGCAAACTAGACACGTGAAGAATTACCATTCAAGATCAGAGTCGACAGTGGAGAACTTCCTGTGCAGATCTGCATGCGTCTTCTACACCACATACAAGAACCATGACTCCGATGGCGACACTTCGCCTACTGGGTGATCAACACACGGCAAGTTGCTCAACTGCGTCGGAAGCTCGAAATGTTCACGT |
| 42 | SVD_1 | FORWARD PRIMER | CAGGATAATTTCTTCCAAGGGC |
| 43 | SVD_1 | REVERSE PRIMER | ACGTGAACATTTCGAGCTTCC |
| 44 | SVD_1 | PROBE | TGCATTGTGTCTGATGGTACAACTTGTGACG |
| 45 | SVD_2 | SIGNATURE SEQUENCE 281 bp | GACTTGTTGTGGCTGGAGGACGACGCCATGGAGCAAGGAGTTAGGGATTATGTGGAACAACTCGGCAACTGCTTCGGCTCAGGATTCACCAATCAAATTTGCGAACAGGTTACCCTTCTAAAAGAGTCGTTAATTGGACAGGATTCTATCCTTGAGAAGTCTCTCAAGGCCCTCGTCAAGATAGTATCAGCACTCGTGATCGTGGTGAGAAATCACGATGACCTCATTACGGTCACCGCCACACTGGCGTTAATAGGATGCACTACCTCACCATGGCGCTG |
| 46 | SVD_2 | FORWARD PRIMER | GACTTGTTGTGGCTGGAGGA |
| 47 | SVD_2 | REVERSE PRIMER | CAGCGCCATGGTGAGGTAG |
| 48 | SVD_2 | PROBE | TGACCGTAATGAGGTCATCGTGATTTCTCAC |
| 49 | SVD_3 | SIGNATURE SEQUENCE 248 bp | GACAAAGTGGCCAAGGGAAAGTCCAGGCTCATCGAGGCTTCTAGCCTCAACGACTCAGTAGCAATGAGGCAGACATTTGGAAACCTATATAAGACTTTCCACCTCAACCCGGGCATCGTTACGGGTAGCGCCGTTGGGTGTGACCCAGATGTCTTTTGGAGCAAGATTCCCGTCATGCTCGATGGACATCTCATAGCGTTTGACTATTCAGGCTATGACGCCAGCCTCAGCCCAGTGTGGTTTACGTG |

TABLE 1-continued

Signature sequences, PCR primers, and probes for detection of 7 agricultural pathogens in a sample.

| SEQ ID NO: | Pathogen_Assay | description | Sequence 5' => 3' |
|---|---|---|---|
| 50 | SVD_3 | FORWARD PRIMER | GACAAAGTGGCCAAGGGAAA |
| 51 | SVD_3 | REVERSE PRIMER | CACGTAAACCACACTGGGCT |
| 52 | SVD_3 | PROBE | CTGGCGTCATAGCCTGAATAGTCAAACGCTA |
| 53 | VESV_1 | SIGNATURE SEQUENCE 153 bp | GCCTTCTCCCTTCCCAAAACGGACGGACCCACCGGAAACGAACCCGAATTCATCGCTGAGGCTTGCCCTAGCTGCGCTCTTTACGACACGTGTCCAAATTGCACATCTAAGGTTATCAACGATGATGGCTCAACTGACGGAACCATTCCTTCA |
| 54 | VESV_1 | FORWARD PRIMER | GCCTTCTCCCTTCCCAAAA |
| 55 | VESV_1 | REVERSE PRIMER | TGAAGGAATGGTTCCGTCAGT |
| 56 | VESV_1 | PROBE | CATCATCGTTGATAACCTTAGATGTGCAATTTGG |
| 57 | VESV_3 | SIGNATURE SEQUENCE 199 bp | GGGAATGAGGTGTGCATCATTGATGAATTCGACTCATCTGACAAGGTTGATTATGCCAATTTTGTAGTCAACATGGTTAACACCAACCCCATGGTCTTAAATTGTGATCTAATTGAAAACAAAGGCAAGACATTCACCTCAAAATACGTCATCATGACGTCCAACACGGAAACACCAGTCAAGCCAACATCAAGACGTG |
| 58 | VESV_3 | FORWARD PRIMER | GGGAATGAGGTGTGCATCATT |
| 59 | VESV_3 | REVERSE PRIMER | CACGTCTTGATGTTGGCTTGAC |
| 60 | VESV_3 | PROBE | AAATTGGCATAATCAACCTTGTCAGATGAGTCG |
| 61 | VESV_4 | SIGNATURE SEQUENCE 124 bp | GGTCGCTCTCACTGATGATGAGTACAATGATTGGAAACAGTCCAAAGCTGAAAAAAACCTCGACCTCACGGTCAAGGACTTCCTCCAACTCAGGCACCGAGCTGCAATGGGTGCTGATAACACC |
| 62 | VESV_4 | FORWARD PRIMER | GGTCGCTCTCACTGATGATGAGTA |
| 63 | VESV_4 | REVERSE PRIMER | GGTGTTATCAGCACCCATTGC |
| 64 | VESV_4 | PROBE | GCTCGGTGCCTGAGTTGGAGGAAG |
| 65 | VESV_5 | SIGNATURE SEQUENCE 200 bp | ACCACCTCTGGAAACATCTATGGAGCCTGCGGCTCATCGTGTTCACTGACGAGACAGGGTGACTGCGGTCTCCCCTACGTCGACGATCACGGTGTTGTCGTTGGACTCCATGCTGGGTCTGGTGGTGACAAATGCCCGTCCCGAAAACTCATTGTTCCCTACGTCAAGGTGGATATGAGAATTCGTGACACGTGCACAAA |
| 66 | VESV_5 | FORWARD PRIMER | ACCACCTCTGGAAACATCTATGG |
| 67 | VESV_5 | REVERSE PRIMER | TTTGTGCACGTGTCACGAAT |
| 68 | VESV_5 | PROBE | CGGGACGGGCATTTGTCACCA |

Accordingly one aspect of the invention is a kit for determining the presence or absence in a sample of at least one pathogen selected from the group consisting of BVH, BPSV, BVD, BTV; SVD; and VESV, said kit having nucleic acid reagents for detection of at least one nucleic acid signature sequence from each pathogen. The following nucleic acid signature sequences are detected: for pathogen BVH, signature sequences consisting of SEQ ID NO:1 or SEQ ID NO:5; for pathogen BPSV, signature sequences consisting of SEQ ID NO:9 or SEQ ID NO:13 or SEQ ID NO:17; for pathogen BVD, signature sequences consisting of SEQ ID NO:29; for pathogen BTV, signature sequences consisting of SEQ ID NO:33 or SEQ ID NO:37; for pathogen SVD, signature sequences consisting of SEQ ID NO:41 or SEQ ID NO:45 or SEQ ID NO:49; and for pathogen VESV, signature sequences consisting of SEQ ID NO:53 or SEQ ID NO:57 or SEQ ID NO:61 or SEQ ID NO: 65.

In one embodiment, the kit further includes reagents for determining the presence or absence FMDV in a sample. The reagents detect at least one nucleic acid signature sequence for FMDV. Example signature sequences include those disclosed in Example 10, below. In other embodiment, FMDV signature sequences are those previously disclosed, e.g., SEQ ID NO:21 (JAVMA, Vol 220, No. 11, Jun. 1, 2002) and/or SEQ ID NO:25 (Journal of Virological Methods 105, (2002), 67-80).

In one aspect, the kit includes reagents for determining the presence or absence of all seven agricultural pathogens, e.g., BVH, BPSV, FMDV; BVD, BTV; SVD; and VESV in a sample. The kit includes nucleic acid reagents for detection of all signature sequences listed in Table 1.

In another aspect, the kits includes reagents for detection of less than all seven pathogens, e.g., for detection of at least 1, 2, 3, 4, 5 or at least 6 of the pathogens.

In some embodiments, the kits include nucleic acid reagents that are sets of oligonucleotides for each signature sequence to be detected. Each set has PCR primers and hybridization probes for each signature sequence. Exemplary embodiments include the PCR primers and hybridization probes disclosed in Table 1. In one embodiment the kit includes each of the PCR primers and hybridization probes listed for the respective pathogen. In other embodiments, the kit includes a subset of the disclosed primer and probes, e.g., at least 1, 2, 3, 4, 5, 6, 7, 8, 9, 10, 11, 12 13, 14, 15, or at least 16 of the primer probe sets disclosed in Table 1.

In one aspect the kits include control nucleic acid reagents. Exemplary control nucleic acid reagents are disclosed in Table 1.

In one variation of the invention, the kit includes hybridization probes that are affixed to a solid substrate, e.g., a microsphere.

Also disclosed are methods using the kits disclosed herein. In some embodiments, the method includes a PCR based amplification step.

Accordingly, in a preferred embodiment the invention provides the use of all PCR primers in Table 1. Alternatively, the invention provides the use of all PCR primers for a particular pathogen. In yet another embodiment the invention provides the use of all of the probes in Table 1. Alternatively, the invention provides the use of all probes in Table 1.

Samples

The invention provides kits and methods for detection of agricultural pathogens in a sample. As will be appreciated by those in the art, the sample may comprise any number of things, including, but not limited to, bodily fluids (including, but not limited to, blood, nasopharyngeal secretions, urine, serum, lymph, saliva, milk, anal and vaginal secretions, and semen) of virtually any organism, with mammalian samples, including livestock, (e.g. sheep, cow, horse, pig, goat, lama, emu, ostrich or donkey), poultry (e.g. chicken, turkey, goose, duck, or game bird), fish (e.g. salmon or sturgeon), laboratory animal (e.g. rabbit, guinea pig, rat or mouse) companion animal (e.g. dog or cat) or a wild animal in captive or free state, being preferred, environmental samples (including, but not limited to, air, agricultural, water and soil samples); biological warfare agent samples; research samples; purified samples, such as purified genomic DNA, RNA, proteins, etc.; and raw samples (bacteria, virus, genomic DNA, etc.). As will be appreciated by those in the art, any experimental manipulation can have been performed on the sample before analysis.

In one embodiment, the sample type for diagnosis of vesicular diseases is vesicular epithelium/fluid. The vesicular diseases include FMD, VESV, SVD, and BVD (if oral lesions are present), parapox (BPSV), and BHV-1 (IBR). In other embodiments, the methods of the invention are performed using sample types including oral/nasal swabs and probang samples, for detection of, e.g., FMD, BVD, and BVH. For detection of BTV (vector-borne), the sample can be is EDTA whole blood. For BVD where no lesions are present, sample types include, e.g., tonsils (scrapings), lymph nodes and spleen.

Additional tissue samples include brain (brain stem, cerebullum, brain stem), spinal cord tissues or fluids, bone marrow, and ear notches.

If required, nucleic acid from the sample is isolated using known techniques. For example, the sample may be treated to lyse the cells, using known lysis buffers, sonication, electroporation, etc., with purification occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents that may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Signature Sequences

Using the kits and methods of the invention, the presence or absence of an agricultural pathogen in a sample is determined using reagents for detection of a signature nucleic acid sequence. The term "signature sequence" or "signature nucleic acid" or grammatical equivalents herein means a nucleic acid sequence on a single strand of nucleic acid or its complement. The signature sequence may be a portion of a gene, a regulatory sequence, genomic DNA, cDNA, RNA including mRNA and rRNA, and the like.

The signature sequences detected are presented in Table 1.

As will be appreciated by those in the art, the signature sequence can take many forms. For example, it may be contained within a larger nucleic acid sequence, i.e. all or part of a gene or mRNA, a restriction fragment of a plasmid or genomic DNA, among others.

Amplification Methods

In one embodiment and as describe more fully herein, a signature sequence from a sample is amplified to produce a secondary target, e.g. an amplicon that is detected, as outlined herein.

Amplification involves the amplification (replication) of the signature sequence to be detected, such that the number of copies of the signature sequence is increased. Suitable amplification techniques include, but are not limited to, the polymerase chain reaction (PCR), strand displacement amplification (SDA), transcription mediated amplification (TMA) and nucleic acid sequence based amplification (NASBA).

In one embodiment, the amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", "allele-specific PCR", among others.

In another embodiment, the amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In another embodiment, the amplification technique is nucleic acid sequence based amplification (NASBA). NASBA is generally described in U.S. Pat. No. 5,409,818; Sooknanan et al., Nucleic Acid Sequence-Based Amplification, Ch. 12 (pp. 261-285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In another embodiment, the amplification technique is signal amplification. Signal amplification involves the use of limited number of target molecules as templates to either generate multiple signaling probes or allow the use of multiple signaling probes. Signal amplification strategies include LCR, CPT, QβR, invasive cleavage technology, and the use of amplification probes in sandwich assays.

In another embodiment, single base extension (SBE; sometimes referred to as "minisequencing") is used for amplification. Briefly, SBE is a technique that utilizes an extension primer that hybridizes to the target nucleic acid. A polymerase (generally a DNA polymerase) is used to extend the 3' end of the primer with a nucleotide analog labeled a detection label as described herein. Based on the fidelity of the enzyme, a nucleotide is only incorporated into the extension primer if it is complementary to the adjacent base in the target strand. Generally, the nucleotide is derivatized such that no further extensions can occur, so only a single nucleotide is added. However, for amplification reactions, this may not be necessary. Once the labeled nucleotide is added, detection of the label proceeds as outlined herein. See generally Sylvanen et al., Genomics 8:684-692 (1990); U.S. Pat. Nos. 5,846,710 and 5,888,819; Pastinen et al., Genomics Res. 7(6):606-614 (1997); all of which are expressly incorporated herein by reference.

In another embodiment, the signal amplification technique is OLA (oligonucleotide ligation amplification). OLA, which is referred to as the ligation chain reaction (LCR) when two-stranded substrates are used, involves the ligation of two smaller probes into a single long probe, using the target sequence as the template. In LCR, the ligated probe product becomes the predominant template as the reaction progresses. The method can be run in two different ways; in a first embodiment, only one strand of a target sequence is used as a template for ligation; alternatively, both strands may be used. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; WO 97/31256; and WO 89/09835, and U.S. Ser. Nos. 60/078,102 and 60/073,011, all of which are incorporated by reference.

In another embodiment the signal amplification technique is RCA. Rolling-circle amplification is generally described in Baner et al. (1998) Nuc. Acids Res. 26:5073-5078; Barany, F. (1991) Proc. Natl. Acad. Sci. USA 88:189-193; and Lizardi et al. (1998) Nat. Genet. 19:225-232, all of which are incorporated by reference in their entirety.

A second alternative approach involves OLA followed by RCA. In this embodiment, an immobilized primer is contacted with a target nucleic acid. Complementary sequences will hybridize with each other resulting in an immobilized duplex. A second primer is contacted with the target nucleic acid. The second primer hybridizes to the target nucleic acid adjacent to the first primer. An OLA assay is performed as described above. Ligation only occurs if the primers are complementary to the target nucleic acid. When a mismatch occurs, particularly at one of the nucleotides to be ligated, ligation will not occur. Following ligation of the oligonucleotides, the ligated, immobilized, oligonucleotide is then hybridized with an RCA probe. This is a circular probe that is designed to specifically hybridize with the ligated oligonucleotide and will only hybridize with an oligonucleotide that has undergone ligation. RCA is then performed as is outlined in more detail below.

Nucleic Acid Reagents: Primers and Probes

The kits and method disclosed herein use nucleic acid reagents, e.g., oligonucleotides, e.g., amplification primers and hybridization probes, for detection of the signature sequences. Exemplary primers and hybridization probes are disclosed herein, e.g., in Table 1, and in one embodiment, the claimed kits and methods include the primers and probes disclosed in Table 1. The invention also include kits and methods using variant versions of the primers and probes disclosed herein, e.g., oligonucleotides that are shorter or longer or have at least 95%, 96%, 97%, 98%, or at least 99% sequence identity, as long as the oligonucleotide accomplishes that same function, e.g., functions in the assay for the detection of the signature sequences.

In addition, one of skill can readily design additional primers and hybridization probes that can function as nucleic acid reagents for the detection of signature sequences. Generally the nucleic acid reagents include signature sequence, or complementary sequence, sufficient to confer specific amplification or hybridization to the target nucleic acid, e.g., agricultural pathogen nucleic acid.

The length of a nucleic acid reagent, e.g., a primer or hybridization probe, will vary depending on the application. In general, the total length can be from about 8 to 80 nucleobases in length. The primers and hybridization probes used in accordance with this invention preferably comprise from about 8 to about 80 nucleobases (i.e. from about 8 to about 80 linked nucleosides). One of ordinary skill in the art will appreciate that the invention embodies oligonucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

Nucleic Acid Reagents: Adapters

In a preferred embodiment, a hybridization probe further comprises an adapter sequence. Adapters facilitate immobilization of probes to solid supports. That is, arrays (either solid phase or liquid phase arrays) are generated that contain capture probes that are not target specific, but rather specific to individual (preferably) artificial adapter sequences. The adapter sequences of the probes are preferably from 15-25 nucleotides in length, with 20 being especially preferred. The target specific portion of the probe is preferably from 15-50 nucleotides in length.

Thus, an adapter sequence is a nucleic acid that is generally not identical to or complementary to the signature sequence, i.e. is exogenous, but is added or attached to a hybridization probe. It should be noted that in this context, the signature sequence can include the primary signature sequence, or can be a derivative target such as a reactant or product of the reactions outlined herein; thus for example, the target sequence can be a PCR product, a first ligation probe or a ligated probe in an OLA reaction, etc.

The terms "barcodes", "adapters", "addresses", "tags" and "zip codes" have all been used to describe artificial sequences that are added to amplicons to allow separation of nucleic acid fragment pools. One preferred form of adapters is hybridization adapters. In this embodiment adapters are chosen so as to allow hybridization to the complementary capture probes on a surface of an array. In general, sets of adapters and the corresponding capture probes on arrays are developed to minimize cross-hybridization with both each other and other components of the reaction mixtures, including the signature sequences and sequences on the larger nucleic acid sequences outside of the target sequences (e.g. to sequences within genomic nucleic acid of the agricultural pathogen).

As will be appreciated by those in the art, the attachment, or joining, of the adapter sequence to the target sequence can be done in a variety of ways. In a preferred embodiment, the adapter sequences are added to the primers of the reaction (extension primers, amplification primers, readout probes, genotyping primers, Rolling Circle primers, etc.) during the chemical synthesis of the primers. The adapter then gets added to the reaction product during the reaction; for example, the primer gets extended using a polymerase to form the new target sequence that now contains an adapter sequence. Alternatively, the adapter sequences can be added enzymatically. Furthermore, the adapter can be attached to the target after synthesis; this post-synthesis attachment can be either covalent or non-covalent. In a preferred embodiment the adapter is added to the target sequence or associated with a particular allele during an enzymatic step.

In addition, as will be appreciated by those in the art, the adapter can be attached either on the 3' or 5' ends, or in an internal position, depending on the configuration of the system.

In one embodiment the use of adapter sequences allow the creation of more "universal" surfaces; that is, one standard array, comprising a finite set of capture probes can be made and used in any application. The end-user can customize the array by designing different soluble target probes, which, as will be appreciated by those in the art, is generally simpler and less costly. In a preferred embodiment, an array of different and usually artificial capture probes are made; that is, the capture probes do not have complementarity to known target sequences. The adapter sequences can then be incorporated in the target probes.

As will be appreciated by those in the art, the length of the adapter sequences will vary, depending on the desired "strength" of binding and the number of different adapters desired. In a preferred embodiment, adapter sequences range from about 5 to about 25 basepairs in length, with 20 being especially preferred.

In a preferred embodiment, the adapter sequence uniquely positions the target analyte, e.g. agricultural organism nucleic acid, to which the target probe binds. That is, while the adapter sequence need not bind itself to the target analyte, the system allows for identification of the target analyte by detecting the presence of the adapter. Accordingly, following a binding or hybridization assay and washing, the probes including the adapters are amplified. Detection of the adapter then serves as an indication of the presence of the target analyte.

Detection of Nucleic Acids

As described herein, the kits and method described herein utilize detection of the signature sequences by detection of amplicons. In general, either direct or indirect detection of amplicon can be performed. Direct detection generally involves the incorporation of a label into the amplicon via, e.g., a labeled primer. Indirect detection involves incorporation of a label into, e.g., a hybridization probe.

For direct detection, the label(s) may be incorporated in four ways: (1) the primers comprise the label(s), for example attached to the base, a ribose, a phosphate, or to analogous structures in a nucleic acid analog; (2) modified nucleosides that are modified at either the base or the ribose (or to analogous structures in a nucleic acid analog) with the label(s); these label-modified nucleosides are then converted to the triphosphate form and are incorporated into the newly synthesized strand by a polymerase; (3) modified nucleotides are used that comprise a functional group that can be used to add a detectable label; or (4) modified primers are used that comprise a functional group that can be used to add a detectable label. Any of these methods result in a newly synthesized strand that comprises labels that can be directly detected as outlined below.

For indirect detection, the label is incorporated into the hybridization probe using methods well known to one of skill in the art. For example, the label can be incorporated by attaching the label to a base, ribose, phosphate, or to analogous structures in a nucleic acid analog, or by synthesizing the hybridization probe using a modified nucleoside.

Thus, a modified strands of the amplicon or the hybridization probe can include a detection label. By "detection label" or "detectable label" herein is meant a moiety that allows detection. This may be a primary label or a secondary label.

In one embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, alexa dyes, phycoerythrin, bodipy, and others described in the 6th Edition of the Molecular Probes Handbook by Richard P. Haugland, hereby expressly incorporated by reference.

In another embodiment, a secondary detectable label is used. Accordingly, detection labels may be primary labels (i.e. directly detectable) or secondary labels (indirectly detectable). A secondary label is one that is indirectly detected; for example, a secondary label can bind or react with a primary label for detection, or may allow the separation of the compound comprising the secondary label from unlabeled materials, etc. Secondary labels find particular use in systems requiring separation of labeled and unlabeled probes, such as SBE reactions. Secondary labels include, but are not limited to, one of a binding partner pair; chemically modifiable moieties; nuclease inhibitors, etc.

In another embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smallest of the pair is attached to the NTP for incorporation into the extension primer.

In another embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In another embodiment, the binding partner pair comprises a primary detection label (for example, attached to the NTP and therefore to the extended primer) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

Formats

Detection of the amplified products described above preferably employs arrays, as described herein. In one embodiment, the arrays comprise hybridization probes affixed to a solid support.

By "substrate" or "solid support" or other grammatical equivalents herein is meant any material to which a hybridization probe can be immobilized. Possible substrates include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, and a variety of other polymers. In general, the substrates allow optical detection and do not themselves appreciably fluoresce.

Generally the substrate is flat (planar), although as will be appreciated by those in the art, other configurations of substrates may be used as well.

In a preferred embodiment the array is a liquid array. In this embodiment, a species of hybridization probes is immobilized to a first set of microspheres. Likewise, a second species of hybridization probes is immobilized to a second set of microspheres. Similarly additional species of hybridization probes are attached to discrete populations of microspheres. There is no upward limit to the number of populations of microspheres or capture probes when populations are analyzed individually.

When multiple sets of microspheres are mixed and analyzed the number of sets is limited only by the number of encoding moieties applied to the microspheres. That is, microspheres are encoded so that the identity of each set of microspheres can be determined. Encoding moieties can be any distinguishable characteristic, e.g. size, shape, texture etc., of the microsphere. In preferred embodiments, encoding moieties are attributes that are not inherent in the bead or microsphere itself. Rather, the encoding moiety is a feature that is added to a bead. Preferred encoding moieties include, but are not limited to nucleic acids, proteins, and detectable labels or fluors. In addition, materials such as nanocrystals can be used as encoding moieties.

Also, in some embodiments, a plurality of different types of encoding moieties can be used to develop numerous different codes.

In a preferred embodiment, the beads and encoding system are those used in the Luminex flow cytometer. This system is described in more detail in U.S. Pat. No. 5,981,180, which is expressly incorporated herein by reference.

Briefly, the flow cytometer comprises a Luminex LX100 Flow Cytometer instrument with a sheath source and a waste reservoir. The hybridized bead array is introduced into the Luminex Flow Cytometer instrument where the beads are interrogated by two lasers, a red laser for the internal discriminator and a green laser for the external discriminator dyes respectively.

With the liquid arrays it is possible to simultaneously multiplex 100 or more different organisms or targets. The discrimination of the polystyrene Luminex bead array is dependent on the precise ratio of two internal discriminator dyes, a red and an infrared dye. The signal intensity on the surface of the bead is dependent on the concentration of the analyte in solution, in our case the amplified DNA of a suspect agent or an antigen or a toxin, whichever the case may be.

A 100-plex Luminex liquid array is generated by intercalating varying ratios of red and orange infrared dyes into polystyrene latex microspheres or beads. The process of producing varying ratios of red and orange infrared dyes in the beads is accomplished by increasing the amount of red dye and increasing the amount of orange dye. This gives each optically encoded bead a unique spectral address.

The beads are coated with capture probes complementary to adapter sequences, e.g., hybridization probes, as described herein. Each bead has an attachment site specific for a unique bioagent, e.g., hybridization probe.

The beads are analyzed in the flow cytometer, one at a time. A red laser classifies the bead, identifying the bead type. Subsequently a green laser quantifies the assay on the bead surface—only those beads with a complete sandwich will produce a fluoresce in the green, and the signal is a function of label concentration, which is indicative of the amount of target, e.g., amplicon.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B (1992); "Oligonucleotide Synthesis" (M. J. Gait, ed., 1984); "Animal Cell Culture" (R. I. Freshney, ed., 1987); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Summary of Assay Development

The Bioassays and Signatures Program (BSP) at Lawrence Livermore National Laboratory (LLNL) have constructed a robust technical architecture for the rapid development of highest-quality nucleic acid assays, tailored to end-user specifications. A summary of this process is shown in FIG. 1.

The pipeline process begins with an analysis of all available genomic sequence information, which forms the basis for the development of signatures. A signature is a region or set of regions on a chromosome that is unique to that organism. Candidate signatures can be selected based on performance criteria for specific detection technologies. Our nucleic acid assays employ PCR with primer pairs to generate the signature fragment(s) of interest. Once candidate signatures have been identified, they are subjected to a computational screening and down-selection process. This "in silico" screening method tests the candidate regions for uniqueness when compared to all the sequence data available. The computational screening also ensures that the signature primer pairs are amenable to assay chemistry requirements and provides rapid, low-cost initial screening of signatures.

The primers that emerge from the computational screening and down-selection are then tested against an extensive panel of DNAs and cDNAs. The bench screening consists of a panel of 2,000 to 3,000 samples, representing a wide range of organisms and backgrounds. This bench screening ensures that the primers will detect the strain diversity of the pathogen but will not react with the nucleic acids of other organisms that could be present in a sample.

Primer pairs that successfully pass the wet chemistry screening criteria are advanced to the assay development stage. Assay development includes the optimization of detection protocols, so that the assays perform consistently to required specifications on the prototype equipment selected. At the assay development stage, assays are fully characterized by assessing performance against a specified, standardized panel of targets (nucleic acid from various strains of the organism of interest, for which the assay was designed) and near-neighbors (genetically-related organisms), which yields rich data about the sensitivity and specificity of an assay. The results of all this work (from informatics through characterization) is captured in an extensive "certificate of analysis" that provides an assay pedigree. The pedigree comprises the entire history of the assay, including results of screening, metrics of performance such as sensitivity, specificity, and known cross-reactions (if any); all available at a glance, captured in a single data file.

Table 2 provides a summary of the number of signatures that were initially identified, screened in-silico, bench screened, and then screened in a mutiplex format.

TABLE 2

Summary of narrowing the search for signature sequences

| Agent | Initial # of candidate signatures | # of signatures forwarded to Taqman | # of signatures released to multiplex | # of signatures in Mux frozen panel |
|---|---|---|---|---|
| BPSV | 8 | 7 | 4 | 3 |
| BHV | 177 | 101 | 4 | 2 |
| BVD | 1 | 1 | 1 | 1 |
| FMDV | 4 | 4 | 4 | 1 |
| BTV | 8 | 8 | 4 | 2 |
| SVD | 4 | 4 | 4 | 3 |
| VESV | 44 | 20 | 6 | 4 |

Example 1

In-Silico Identification of Candidate Signature Sequences

The LLNL Bioinformatics team developed "KPATH", a whole-genome comparative analysis software system. The general approach is the following: All available complete genomes of different strains of the target species are compared using multiple genome alignment programs. A consensus gestalt is formed from the alignments that contain the sequence conserved among all target inputs. This step is bypassed if only one target sequence is available. To establish that the organism-conserved sequence does not occur in any other sequenced microbial organism, the consensus gestalt is compared against the LLNL updated database of microbial organisms. A customized algorithm accomplishes this electronic subtraction, and the result is a uniqueness gestalt that is mined for potential signature candidates. A final computational screening is done to verify that cross-reactions are not detected.

KPATH allows the genome to define potential signature candidates. However, rather than selecting candidate signatures randomly (often there are more candidates than is economically feasible to screen in the wet lab), they can be prioritized based on annotation. Annotation allows signatures to be scrutinized in a biological context. Identifying genes responsible for rendering a pathogen virulent is one component of a good diagnostic signature set. We manually select candidates associated with genes of interest, and include a random selection of candidates within intergenic regions, for wet lab screening. The random unique intergenic regions are selected as a guard against gene deletion or substitution engineering to evade DNA-based detection. We note that there are few tools focused on viral gene finding, and none known to us that can adequately predict genes in certain RNA virus families.

Because signature candidates are generated using exact matches in the Vmatch step described above, additional electronic screening on the signature candidates is performed to catch potential non-exact matches that might result in false positives in the wet lab. We have seen cases where this would predict cross-reaction with near-neighbor species that had not been caught by the exact-matching step (due to as few as 1 or 2 fortuitously-placed mis-matched bases.)

Table 3 summarizes the genomes used to generate candidate signatures for the seven agricultural pathogens.

TABLE 3

Genomes screened via K-path to generate candidate signature sequences for 7 agricultural pathogens

| Pathogen | Genome Description | GI Number | Sequence Length (bp) |
|---|---|---|---|
| BHV | Bovine Herpesvirus 1 | 9629818 | 135301 |
| BPSV | Sequence 1 from Patent WO03006654 | 32167392 | 137560 |
| BPSV | raw sequence of Orf virus OV-IA82 from Dan Rock on Oct. 21, 2003 | 40019122 | 137241 |
| BPSV | raw sequence of Orf virus OV-SA00 from Dan Rock on Oct. 21, 2003 | 40019123 | 139962 |
| BPSV | raw sequence of Orf virus OV-SA00 from Dan Rock on Oct. 21, 2003 | 40019124 | 134431 |
| BVD | mature peptide N-Pro, proteinase, cleaves itself from the nascent polyprotein | 9626649|NC_001461.1 | 12573 |
| FMDV | Foot-and-mouth disease virus polyprotein, isolate C3Arg85 | 4007041/AJ007347.1 | 8161 |

TABLE 3-continued

Genomes screened via K-path to generate candidate signature sequences for 7 agricultural pathogens

| Pathogen | Genome Description | GI Number | Sequence Length (bp) |
|---|---|---|---|
| FMDV | Foot-and-mouth disease virus, derived from C3Arg85, clone 15 | 4007043/AJ007572.1 | 8161 |
| FMDV | Foot-and-mouth disease virus (FMDV) strain C, isolate c-s8c1 | 6318187/AJ133357.1 | 8115 |
| FMDV | Foot-and-mouth disease virus (FMDV) strain C, isolate rp99 | 6318189/AJ133358.1 | 8115 |
| FMDV | Foot-and-mouth disease virus (FMDV) strain C, isolate rp146 | 6318191/AJ133359.1 | 8115 |
| FMDV | Foot-and-mouth disease virus C strain C-S8 clone MARLS, | 10334811/AF274010.1 | 8115 |
| FMDV | FMDV RNA of primary translation product | 61063/X00429.1 | 7107 |
| FMDV | Foot & mouth disease virus A12; L, P2, and P3 polypeptide coding region | 210306/M10975.1 | 7712 |
| FMDV | Foot and Mouth Disease Virus A L-fragment of RNA genome | 397965/X74812.1 | 7820 |
| FMDV | Foot and mouth disease virus (FMDV-O1K) RNA for polyprotein precursor | 61076/X00871.1 | 7804 |
| FMDV | Foot-and-mouth disease virus (strain O1) polyprotein gene | 6456593/AF189157.1 | 6996 |
| FMDV | Foot-and-mouth disease virus polyprotein precursor | 5031481/AF154271.1 | 7739 |
| FMDV | Foot-and-mouth disease virus O strain Chu-Pei complete genome | 5921457/AF026168.2 | 7733 |
| FMDV | Foot-and-mouth disease virus, complete genome | 12018088/AF308157.1 | 8134 |
| FMDV | Foot-and-mouth disease virus C, complete genome | 10445391/NC_002554.1 | 8115 |
| BTV | Bluetongue virus (serotype 17/isolate USA) segment 1 from LLNL on Feb. 14, 2005 1:58 PM | Segment 1 reference genome: 50253391/NC006023.1 | 3862 |
| BTV | Bluetongue virus (serotype 10/American isolate) segment 1 from LLNL on Feb. 14, 2005 1:51 PM | Segment 1 reference genome: 50253391/NC006023.1 | 3703 |
| BTV | Bluetongue virus (serotype 2/isolate USA) segment 1 from LLNL on Feb. 14, 2005 2:01 PM | Segment 1 reference genome: 50253391/NC006023.1 | 3857 |
| BTV | Bluetongue virus (serotype 11/isolate USA) segment 1 from LLNL on Feb. 14, 2005 1:53 PM | Segment 1 reference genome: 50253391/NC006023.1 | 3755 |
| BTV | Bluetongue virus (serotype 13/isolate USA) segment 1 from LLNL on Feb. 14, 2005 1:56 PM | Segment 1 reference genome: 50253391/NC006023.1 | 3830 |
| BTV | Bluetongue virus (serotype 17/isolate USA) segment 8 from LLNL on Feb. 14, 2005 2:00 PM | Segment 8 reference genome: 50253377/NC_006007. | 1074 |
| BTV | Bluetongue virus (serotype 10/American isolate) segment 8 from LLNL on Feb. 14, 2005 1:51 PM | Segment 8 reference genome: 50253377/NC_006007. | 1085 |
| BTV | Bluetongue virus (serotype 11/isolate USA) segment 8 from LLNL on Feb. 14, 2005 1:54 PM | Segment 8 reference genome: 50253377/NC_006007. | 977 |
| BTV | Bluetongue virus (serotype 13/isolate USA) segment 8 from LLNL on Feb. 14, 2005 1:57 PM | Segment 8 reference genome: 50253377/NC_006007. | 1090 |
| BTV | Bluetongue virus (serotype 17/isolate USA) segment 9 from LLNL on Feb. 14, 2005 2:00 PM | Segment 9 reference genome: 50253379/NC_006008.1 | 997 |
| BTV | Bluetongue virus (serotype 10/American isolate) segment 9 from LLNL on Feb. 14, 2005 1:52 PM | Segment 9 reference genome: 50253379/NC_006008.1 | 897 |
| BTV | Bluetongue virus (serotype 2/isolate USA) segment 9 from LLNL on Feb. 14, 2005 2:03 PM | Segment 9 reference genome: 50253379/NC_006008.1 | 1029 |
| BTV | Bluetongue virus (serotype 11/isolate USA) segment 9 from LLNL on Feb. 14, 2005 1:54 PM | Segment 9 reference genome: 50253379/NC_006008.1 | 808 |
| SVD | Swine vesicular disease virus strain NET/1/92, complete genome | 8896132 | 7406 |
| SVD | PISVDV Swine vesicular disease virus complete genomic RNA | 61167 | 7400 |
| SVD | SVDMPS Swine vesicular disease virus gene for polyprotein, complete cds | 37993797 | 7401 |
| SVD | Swine vesicular disease virus strain HK'70, complete genome | 402536 | 7401 |

TABLE 3-continued

Genomes screened via K-path to generate candidate signature sequences for 7 agricultural pathogens

| Pathogen | Genome Description | GI Number | Sequence Length (bp) |
|---|---|---|---|
| SVD | Swine vesicular disease virus (STRAIN H/3 '76) genomic RNA, complete genome | 1228947 | 7401 |
| VESV | Vesicular exanthema of swine virus, complete genome | 10314005/NC_002551.1 | 8284 |

Example 2

Use of Taqsim to Further Screen Candidate Signature Sequences

A computational TaqMan simulator program, "Taqsim", was used to identify all potential targets for each candidate signature from all sequences available in Genbank. Taqsim is a BLAST-based comparison of each signature as a triplet against all sequences in Genbank to identify the targets that are predicted to produce a TaqMan reaction at 57 degrees primer annealing and 67 degrees for probe annealing (these temperatures are according to Primer 3 oligo Tm calculations). Input parameters allow for standardized signature informatics that allows for universal protocol development and assay compatibility.

TABLE 4

Taqsim settings used for generation of candidate signatures
Primer3 Parameters

| Parameters | Standard Settings |
|---|---|
| PRIMER_OPT_SIZE | 20 |
| PRIMER_MIN_SIZE | 18 |
| PRIMER_MAX_SIZE | 27 |
| PRIMER_PRODUCT_OPT_SIZE | 100 |
| PRIMER_PRODUCT_SIZE_RANGE | 71-600 |
| PRIMER_OPT_TM | 62 |
| PRIMER_MIN_TM | 61 |
| PRIMER_MAX_TM | 63 |
| PRIMER_MIN_GC | 20 |
| PRIMER_MAX_GC | 80 |
| PRIMER_PICK_INTERNAL_OLIGO | 1 |
| PRIMER_INTERNAL_OLIGO_OPT_SIZE | 31 |
| PRIMER_INTERNAL_OLIGO_MIN_SIZE | 18 |
| PRIMER_INTERNAL_OLIGO_MAX_SIZE | 36 |
| PRIMER_INTERNAL_OLIGO_OPT_TM | 72 |
| PRIMER_INTERNAL_OLIGO_MIN_TM | 71 |
| PRIMER_INTERNAL_OLIGO_MAX_TM | 73 |
| Number of Primers/Probe Set generated: | 101 |

Example 3

Wet Chemistry Screening Process

To ensure extremely high selectivity and sensitivity, a rigorous wet-chemistry screening was performed to further down-select candidate nucleic acid signatures before taking those signatures that pass this screening on to assay development. This step ensures that the primers will detect the strain diversity of the pathogen, but will not react with the nucleic acids of other organisms that could be present in a sample. At this stage, only the primers are tested and many unsuitable primers (e.g., those that form primer-dimers, those that do not produce amplicons of the correct size, etc.) can be eliminated in this first step.

An initial screening of the PCR signatures was performed in duplicate using end-point PCR and gel electrophoresis as described herein. The signatures are initially screened against nucleic acid extractions from 5 soils, 5 eukaryotic nucleic acids, and 5 microbes, each picked at random, and selected near neighbors. The soils represent a diverse geographical and temporal distribution and contain complex mixtures of organisms. The eukaryotic nucleic acids are those that may potentially carry over from sample collection processes. The microbial nucleic acids were selected to span the range of microbial diversity. Near neighbors are organisms that are closely related at the genetic level and have the greatest likelihood of causing confounding results in the assays.

Signatures that produce amplicons with various soils, microbe, eukaryotic or near neighbor nucleic acids were eliminated. Furthermore, signatures were eliminated due to their inability to produce correct size PCR product when crossed with targets. The down-selected signatures are then put through intensive background screening in real-time (TaqMan) PCR format.

Reagents: Invitrogen Platinum Taq polymerase, Catalog #10966-083 (Carlsbad, Calif.); Invitrogen 10 PCR Buffer, Catalog #10966-083 (Carlsbad, Calif.); Invitrogen 50 mM MgCl2, Catalogue #10966-083 (Carlsbad, Calif.); Sigma Chemical BSA, Catalogue #B8687 (St Louis, Mo.); Amersham dNTPs, Catalogue #27-2035-02 (Piscataway, N.J.); Biosearch Technologies oligonucleotides (Novato, Calif.); Nuclease-Free water; Cambrex 4% agarose gel, Catalogue #57225; Cambrex Simplyload 20 bp ladder, catalogue #50331; Teknova 10×TBE, Catalogue # T0210; Teknova 10× Loading Dye, Catalogue # F3062; Clonetech Powerscript one step qRT-PCR kit, Catalogue #630051.

Sample preparation. Pathogen nucleic acids were isolated from virus grown in cell culture as described herein.

PCR assays for DNA templates: Background templates are added to each 25 ul reaction in the following amounts: 5 ng of total soil extract, 1 ng of total Eukaryotic extracted DNA and 200 pg of total extracted Prokaryotic DNA. Control on each plate consists of 2 *Bacillus thuringiensis* reactions (1 ng DNA per 25 ul reaction), and an NTC (No Template Control=5 ul PCR water in place of the template), for each primer used on the plate. Each reaction includes the following: 10×PCR Buffer (2.5 ul); 10 mM dNTPs (2.0 ul); 50 mM MgSO4 (2.25 ul); BSA (2 ug/ul) (1.0 ul); F/R Primers (2.5 uM) (1.0 ul); PlatinumTaq (0.125.0 ul); PCR water (11.125 ul); Template (in 5.0 ul). Thermalcycler Parameters are as follows: Cycle 1: (1×): Step 1: 94.0° C. for 01:00; Cycle 2: (39×) Step 1: 94.0° C. for 00:20; Step 2: 55.0° C. for 0:10; Step 3: 72.0° C. for 00:30; Cycle 3: (1×) Step 1: 15.0° C., HOLD.

PCR assays for RNA templates: Primer set assays are performed in triplicate against available RNA extractions of targets and near neighbors using 200 pg of extracted RNA to each 25 ul reaction. Each reaction includes the following: 2× One-step RT-PCR Buffer (12.5 ul); 50×Q Taq Polymerase Mix, 1.5 U/ul (0.5 ul); 60×Q PowerScript (0.42 ul); PCR water (5.53 ul); F/R Primers (10 uM) (1.05 ul); Template in 5 ul. Thermalcycler Parameters are as follows: Cycle 1: (1×) Step 1: 48.0° C. for 20:00; Step 2: 95.0° C. for 03:00; Cycle 2: (39×): Step 1: 95.0° C. for 0:15; Step 2: 60.0° C. for 01:00; Step 3: 72.0° C. for 00:15; Cycle 3: (1×): Step 1: 15.0° C. HOLD.

Gel electrophoresis. Product size was determined by running 15 ul of PCR product with 5 ul 10× loading dye (Teknova; Hollister, Calif.) on 4% agarose gels (Cambrex Rockland, Ind.) in Tris-borate-EDTA buffer (Teknova). Band size was determined using Cambrex's Simpleload 20 base pair ladder. The Epi Chemi II Darkroom Bioimaging system (UVP BioImaging Systems Upland, Calif.) was used for visualization of the DNA.

Example 4

Taqman Format Screening

Following the wet screening process, signature sequences were screened in a real-time PCR format in triplicate against nucleic acid samples that include nucleic acid extracts from all targets and near neighbors, 16 eukaryotes, 55 soils, 45 prokaryotes, and a total of 2256 samples collected from aerosol collectors and pooled for background testing purposes. Primer pairs that successfully pass the wet chemistry screening criteria are advanced to the assay development stage.

Taqman assay development includes the bioinformatics selection and evaluation processes, and optimization and characterization. Optimization is conducted for every relevant parameter that impacts assay performance. For example, in a standard RT-PCR assay, parameters to be optimized include: primer/probe length, GC content, Tm, concentration(s), thermocycling parameters (2-step or 3-step, times, temperatures for each step) reaction conditions (MgCl2 concentration), Taq polymerase (type and concentration), reaction buffers, extraction protocols, etc.

Taqman probes: Probes for Real-time PCR Taqman reactions were obtained from Biosearch Technologies using the Tamara fluorophore and Black Hole quencher. In some instances the Taqman probes had the same sequence as the probes used in the multiplex Luminex assay and described in Table 1, e.g., the Taqman probes were forward complement probes (FCP). In other instances, the Taqman probes were the reverse complement of probes disclosed in Table 1 and used in the Luminex assay. For example, for the BHV-1 assay, the sequence of the real-time probes was the reverse complement of the Luminex probe, e.g., the sequence was CTCCATGTTAGCGCTCTGGAACCTGGA. The Taqman probes were as follows:

TABLE 5

Probes for Taqman assays

| SEQ ID NO: | Pathogen-assay | Real-time probe orientation | Sequence (5' => 3') |
|---|---|---|---|
| 69 | BHV-1 | Plus, RCP | CTCCATGTTAGCGCTCTGGAACCTGGA |
| 70 | BHV-3 | Plus, RCP | CGCGAATCTTATTTAAGTGCACACCGTGTTATTT |
| 71 | BPSV-1 | Plus, RCP | CACGTTCTCCACGTCGGAGTCGG |
| 72 | BPSV-2 | Plus, RCP | CGGAAGCCCATGAGCCCGTACA |
| 73 | BPSV-4 | Plus, RCP | CGCTTGTTGTCCGCCTCGAAGTC |
| 74 | BTV-2 | Plus, RCP | ACAGAAGATGATGATTGGCCCACGAGTTAG |
| 75 | BTV-3 | Minus, FCP | CTAACTCGTGGGCCAATCATCATCTTCTGT |
| 76 | BVD-1a(mod) | Plus, RCP | CTCGAGATGCCACGTGGACGAGG |
| 77 | FMDV.Pir | Minus, FCP | CCTCGGGGTACCTGAAGGGCATCC |
| 78 | FMDV.TC | Minus, FCP | GTCCCACGGCGTGCAAAGGA |
| 79 | SVD_1 | Plus, RCP | CGTCACAAGTTGTACCATCAGACACAATGCA |
| 80 | SVD_2 | Minus, FCP | TGACCGTAATGAGGTCATCGTGATTTCTCAC |
| 81 | SVD_3 | Minus, FCP | CTGGCGTCATAGCCTGAATAGTCAAACGCTA |
| 82 | VESV_1 | Plus, RCP | CCAAATTGCACATCTAAGGTTATCAACGATGATG |
| 83 | VESV_3 | Plus, RCP | CGACTCATCTGACAAGGTTGATTATGCCAATTT |
| 84 | VESV_4 | Plus, RCP | CTTCCTCCAACTCAGGCACCGAGC |
| 85 | VESV_5 | Plus, RCP | TGGTGACAAATGCCCGTCCCG |

Sample preparation, DNA: Total DNA was extracted from virus infected cell culture as follows. Add $5\times10^{-2}$ nanograms of Puc18 per ml of virus cell culture (to 15 ml add 0.75 ng Puc19). Add Triton X-100 to a final concentration of 0.5% V/V (to 15 ml add 75 ul Triton). Add 0.5M EDTA to a final concentration of 20 mM (15 ml add 600 ul 0.5M EDTA. Mix vigorously and vortex, let sit 5 min at room temp. Spin tube at <1000 rpm for 10 minutes. Discard pellet and to the supernatant add 10% (W/V) Sodium Dodecyl Sulfate (SDS) solution to a final concentration of 1% (to 15 ml add 1.5 ml of 10% SDS). Add proteinase K to a final concentration of 0.4 Upper ml (to 15 ml add 2.4 mg of 2.5 U/mg Roche or 60 ul of a 0.1 mg/ul solution of proteinase K in water). Incubate the tubes at 55° C. for one hour mixing every 10 minutes. Cool tubes to room temperature. Add 5 M NaCl to a final concentration of 150 mM (to 16.5 ml add 510 ul 5 M NaCl). Add an equal volume of room temperature phenol/chloroform/isoamyl alcohol (approx. 15 ml). Mix by inversion and swirling till phases are completely mixed. Let sit 5 min then spin at 3,000 rpm for 10 min. Remove the upper aqueous layer and distribute 500 ul into 1.5 ml microcentrifuge tubes (for 15 mls need 30 tubes). Discard the lower layer in phenol/chloroform waste. Add two volumes (1 ml) of 100% ethanol to each microcentrifuge tube and leave at −20° C. one hour. Spin in microfuge at top speed refrigerated for 10 minutes. Discard supernatant and wash pellet once with 70% ethanol 150 mM NaCl. Remove all ethanol and dissolve the pellet in TE. For 15 ml extraction dissolve each pellet in each tube in 50 ul of liquid. Each tube should contain 50 fg/ul of puc 18.

Sample preparation, RNA: RNA was extracted from virus infected tissue culture samples as follows. Add 3× the volume Trizol (TRIZOL LS Invitrogen Cat. No. 10296-010) to the volume of sample. (Upon completion of this step, sample can be stored at −80, or continue with extraction.) Lyse cells in the sample suspension by passing the suspension several times through a pipette, or by shaking vigorously. Incubate for 15 minutes at room temperature. (Typically, LLNL uses 2× the volume Trizol to water (e.g., 15 ml sample and 30 mls TRIZOL.) Add 200 ul chloroform per 1 ml solution in the fume hood, cap and shake vigorously for 15 seconds. Incubate at room temperature for 5-15 minutes. Centrifuge at 3000 g for 15 minutes, at 4° C. Remove aqueous layer. Add 1 ml isopropyl alcohol per 500 ml aqueous layer. Gently mix by inverting several times. Incubate samples on the bench top for 10 minutes. Centrifuge at 12,000 g for 10 minutes at 4 C. Carefully, pour off liquid. Wash pellet with 70% EtOH. Vortex sample and re-centrifuge at 7,500 g for 5 minutes at 4° C. Pour off the EtOH, cap, re-spin at 7,500 g for 5 minutes and pipette off remaining liquid. Air dry briefly at 55° C., caution not to over-dry. Resuspend RNA in RNAse-free water and store at −80° C.

Reverse transcriptase. RNA samples were subjected to reverse transcription using the BD Clonetech kit, 48 degrees C. for 30 minutes.

Real-time PCR for DNA samples. Primer/probe set assays were performed in triplicate against 54 extracted soil samples, 16 Eukaryotic backgrounds and 45 Prokaryotic backgrounds and against 3 distinct aerosol extraction plates, adding 5 ul template to each 25 ul reaction. Background templates, with the exception of aerosols, were added to each 25 ul reaction in the following amounts: 5 ng of total soil extract, 1 ng of total Eukaryotic extracted DNA and 200 pg of total extracted Prokaryotic DNA. (The backgrounds are pre-made up in plates that are diluted to the proper concentrations so that 5 ul of each background is added to each 25 ul reaction.) Controls on each plate consist of 2 *Bacillus thuringiensis* reactions (1 ng DNA per, 25 ul reaction), and an NTC (No Template Control=5 ul PCR water in place of a template), reaction for each primer/probe on the plate.

| Component | 1x (ul) |
| --- | --- |
| 10x PCR Buffer | 2.5 |
| 10 mM dNTPs | 0.5 |
| 50 mM MgSO4 | 3.0 |
| BSA (2 ug/ul) | 1.0 |
| F/R Primers (10 uM) | 0.5 |
| Probe (10 uM) | 1.0 |
| PlatinumTaq | 0.25 |
| PCR Water | 11.25 |
| Template (**/ul) | 5.0 |

| iCYCLER Parameters | | |
| --- | --- | --- |
| Cycle 1: (1X) | 95.0° C. for 01:00 | |
| Cycle 2: (39X) | 95.0° C. for 00:20 | Data collection and real-time analysis enabled |
| | 55.0° C. for 00:10 | |
| | 72.0° C. for 00:30 | |
| Cycle 3: (1X) | 4.0° C. HOLD | |

PCR for RNA samples. Reverse transcriptase Real-Time Procedure. Follow steps 1 and 2 of the Real-Time DNA procedure for background screening on each signature. Perform primer set assays in triplicate against RNA extractions of targets and near neighbors using the Clonetech RT-PCR kit. Controls on each plate consist of 2 *Bacillus thuringiensis* (Bt) reactions (1 ng DNA per 25 ul reaction), and an NTC (No Template Control=5 ul PCR water in place of a template), reaction for each primer/probe on the plate. Be sure to use the Clonetech RT-KIT for Bt controls on RNA plates.

| Clontech RT-PCR Reagent Mix Preparation: | |
| --- | --- |
| Component | 1x (ul) |
| 2x One-step RT-PCR Buffer | 12.5 |
| 50x Q Taq Polymerase Mix, 1.5 U/ul | 0.5 |
| 60x Q PowerScript | 0.42 |
| PCR water | 5.33 |
| F/R Primers (10 uM) | 1.05 |
| Probe (10 uM) | 0.20 |
| Template, concentration varies | 5.0 |

| iCYCLER Parameters | | |
| --- | --- | --- |
| Cycle 1: (1X) | 48.0° C. for 20:00 | |
| Cycle 2: (39X) | 95.0° C. for 00:10 | Data collection and real-time analysis enabled |
| | 60.0° C. for 01:00 | |
| | 72.0° C. for 00:15 | |
| Cycle 3: (1X) | 15.0° C. HOLD | |

PCR efficiency. The efficiency, of the PCR assay was determined by testing dilutions from 3000 pg to 10 pg in triplicate. The average ct value was graphed against the template concentration, the equation of the resulting line yielded the R2 value that represents the PCR efficiency.

Signature sequences that performed well in the Taqman format are presented in Table 1.

Example 5

Development of Multiplexed Liquid Array Format

Figure 2:
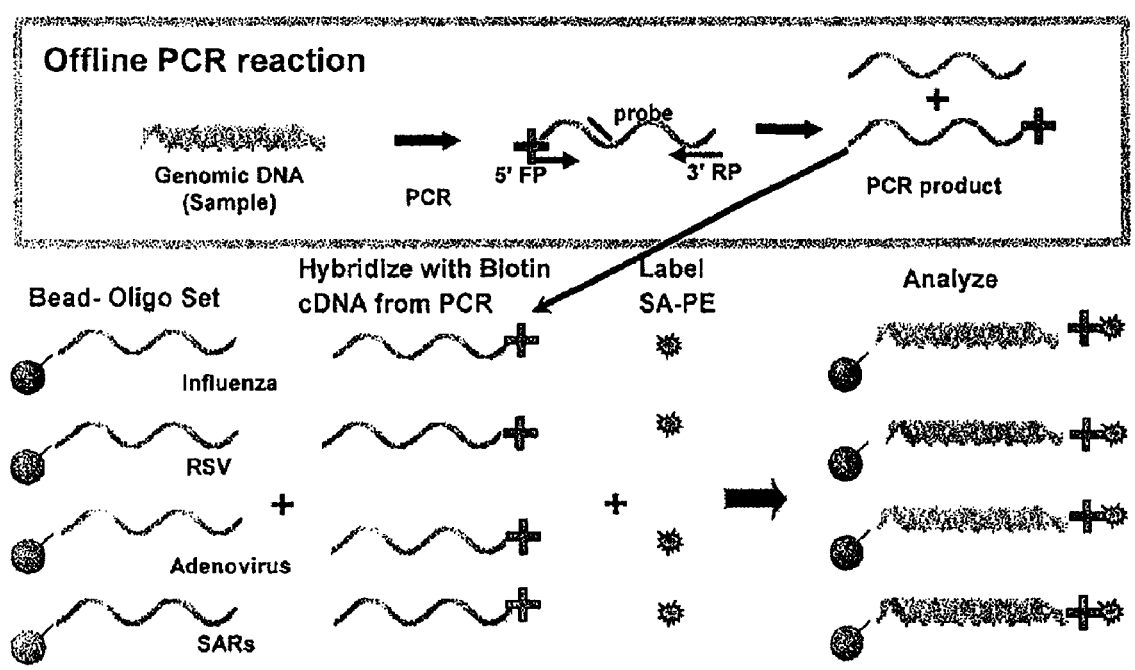
FIG. 2 illustrates one embodiment of detection of signature sequences in a sample via PCR amplification of signature sequences in the target and hybridization to probes covalently coupled to beads. Individual primer pairs (biotinylated forward and standard reverse) that bracket the target genomic sequence are included in an automated PCR master mix of buffers, Taq polymerase, dNTPs, etc. After target amplification by PCR, the amplicons are mixed with beads where target amplicons containing the forward biotinylated primer hybridize to the complementary probe on the appropriate beads. A fluorescent reporter molecule (strepavidin-phycoerythrin) then binds biotin functional groups. Therefore, the completed assay comprises a bead+probe+biotinylated (and fluorescently tagged) amplicon. The sample is then analyzed using a Luminex detector.
Figure 3:
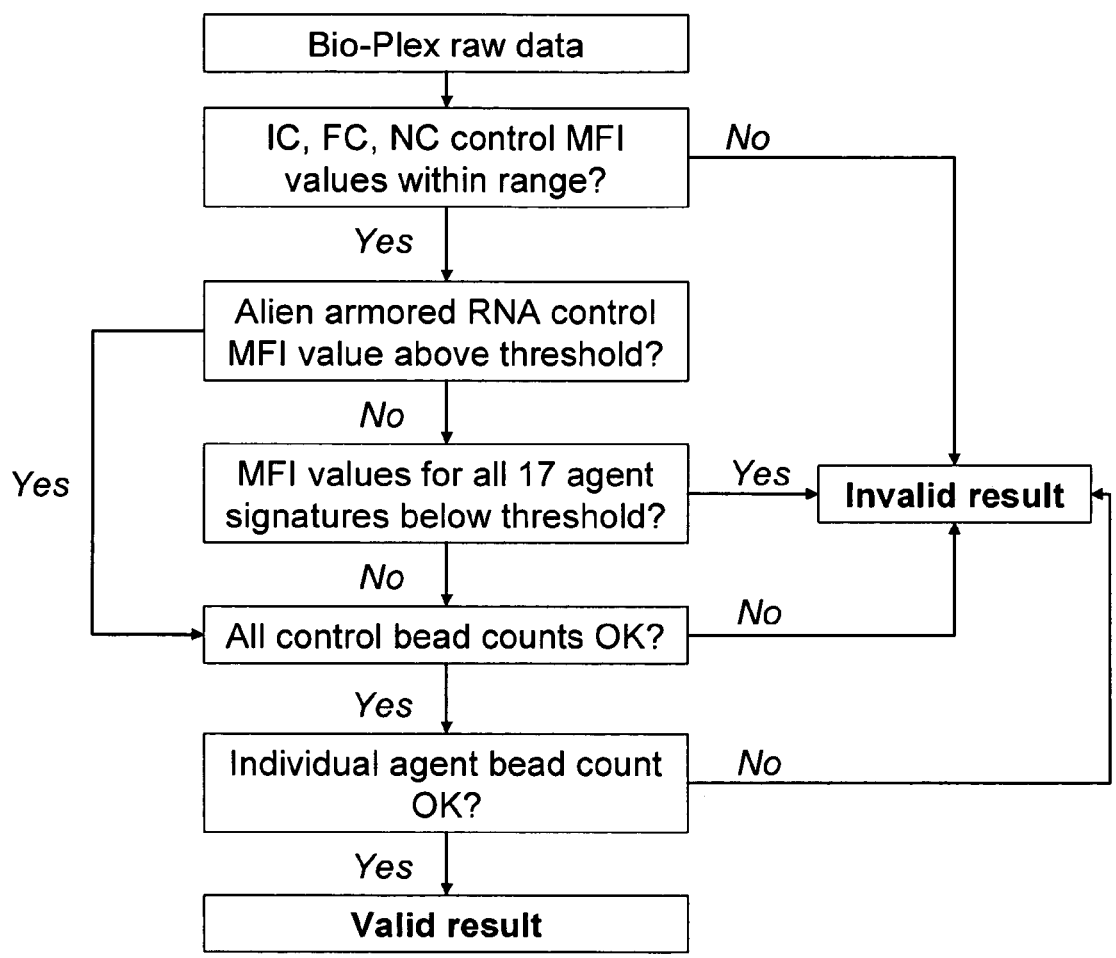
FIG. 3 is a flow diagram illustrating the process used to determine whether or not any individual assay result is valid based on results of the control data.

After ascertaining that signatures perform well in the Taqman format, they are then transitioned to the multiplexed liquid array format. The multiplexes liquid array format is summarized in FIG. 2.

This phase is divided into two steps. The first step, called 'Singlepex' testing, is a step in which each individual signature is tested against target virus. In this format, only two sets of primers are present in the PCR mix: the primers for the Alien RNA positive control (to ensure the PCR reaction proceeds well), and the primers for the signature being tested. The target virus is then spiked at various concentrations in order to generate a titration curve. All titrations are run in triplicate. In the cases in which various strains of the same virus are available, a titration is run for each one.

The second step, called 'Multiplexed' testing, is a step in which the individual signatures are added to the multiplexed panel. In this format, the primers of the signature being tested are added to the multiplexed PCR mix, with the other primers present in the panel. Titrations are then run in triplicate for each signature present in the panel in order to determine the limit of detection of the assay against each target in the multiplexed format, and also to control for signature cross-reactivity.

A summary of the multiplex PCR assay procedure is as follows. The sample, e.g., an oral swab placed in virus transport media, undergoes a magnetic bead extraction to purify target nucleic acids from impurities in the sample matrix. Target DNA or RNA is amplified by real-time-PCR. The forward primer is biotinylated. The reverse primer is unmodified. The double stranded PCR product is mixed with a suspension of probe-bead conjugates then melted at 95° C. to form single strand product. Extended forward primer is hybridized to the complementary probe-bead conjugate at 95° C. The hybridized product is then labeled with the fluorescent probe SA-PE. The bead suspension is analyzed using the flow cytometer.

For this application, oligonucleotide probes with sequences that are complementary to the target nucleic acid sequences were covalently coupled to beads. Nucleic acids from pathogens (targets) were amplified using standard PCR techniques. After target amplification, the amplicons, half of which contain the biotinylated forward (5'-3') primer were introduced to the beads and allowed to hybridize to their complementary probes on the appropriate bead. A fluorescent reporter molecule (strepavidin-phycoerythrin) was added, and binds the biotin functional groups within the forward primer. Therefore, the completed assay product comprises a bead+probe+biotinylated (and fluorescently tagged) amplicon. Each optically encoded and fluorescently-labeled microbead was then interrogated by the flow cytometer. The 635-nm red diode laser excites the dyes inside the bead and classifies each bead to its unique bead class, and a green "reporter" laser (532 nm) quantifies the assay at the bead surface. The flow cytometer is capable of reading several hundred beads each second; analysis can be completed in as little as 15 seconds. Conducting the assay requires multiple steps and significant thermocycling times; the process currently takes about 2 hours.

Extraction of Target Nucleic Acid from a Sample

Extractions of nucleic acid from the samples were conducted with an MagMax (catalog #1839, Ambion, Austin, Tex.) extraction kit using the standard protocol. The kit is specifically designed for the simultaneous extraction of both DNA and RNA using a single procedure. Nucleic acid was extracted from deactivated antigens to use as positives when testing the various signatures.

Primer and Probe Synthesis

Oligonucleotides for Luminex bead-based assays were purchased from Integrated DNA technologies (IDT DNA, Coralville, Iowa). Each forward primer has a 5 prime biotin and 2 internal biotins. Since the biotin molecules are proportionately larger than the bases, it is preferred that the biotins be separated by about 5-10 bases and it is important that there is not a biotin too near the 3 prime terminus of the forward primer, as this could interfere with amplification efficiencies. The reverse primer was unmodified.

The probe was modified with a 5' amine and a space amine modification for coupling the microbeads, e.g., if the real-time PCR probe sequence is 5'FAM-ATCCGCGCATAG-TAM3', the Luminex probe sequence becomes 5'/5AmMC12//iSp18//ATCCGCGCATAG-3'.

A number of oligonucleotide synthesis parameter were optimized for the multiplex, Luminex based assays. First, all oligonucleotides were HPLC purified. A small percentage of probes produced were contaminated by free biotin molecules that are residuals from the primer production. This contamination can cause undesirable interference with the assay. To minimize this occurrence and improve quality control, we have requested that IDT includes a SA (streptavidin agarose) purification followed by sephadex filtration to remove any contamination. We have also found that impurities in the oligonucleotides (synthesis "artifacts"; buffer crystals, truncated products, etc) can also weaken assay performance. As a result we require purity to be a minimum of 85% to pass quality standards with less than 15% impurities. Quality control documentation; signed ESI Mass Spectrometry Trace and Capillary Electrophoresis Trace was required. Oligonucleotides were shipped as lyophilosized pellets and are then resuspended to their desired concentrations; primers in TE [Tris EDTA, pH 8] buffer and probes in 0.1M MES [(2-{N-morpholino}ethanesulfonic acid)] buffer, pH 4.5. All oligonucleotides are stored in small aliquots at –20° C.

TABLE 6

Modified forward primers for Luminex assay

| Pathogen-assay | SEQ ID NO: | Sequence |
|---|---|---|
| BHV-1 | 85 | 5'-/5Bio/G/iBiodT/GCCAGCCGCG/iBiodT/AAAAG-3' |
| BHV-3 | 86 | 5'-/5Bio/TGAGGCc/iBiodT/ATGTATGGGCAG/iBiodT/T-3' |
| BPSV-1 | 87 | 5'-/5Bio/GCAGA/iBiodT/GCGCTCC/iBiodT/GGTT-3' |
| BPSV-2 | 88 | 5'-/5Bio/GATGGCCG/iBiodT/GCAGC/iBiodT/CTT-3' |
| BPSV-4 | 89 | 5'-/5Bio/GCAGCAG/iBiodT/GCACCACG/iBiodT/AGT-3' |
| BTV-2 | 90 | 5'-/5Bio/GCACCC/iBiodT/ATATGTT/iBiodT/CCAGACCA-3' |
| BTV-3 | 91 | 5'-/5Bio/AGAAT/iBiodT/CAGGA/iBiodT/GGGCAGGA-3' |
| BVD-1a(mod) | 92 | 5'-/5Bio/GGTAGTCG/iBiodT/CAGTGGT/iBiodT/CGAC -3' |
| FMDV.Pir | 93 | 5'-/5Bio/CAC YTY AAG R/iBiodT/G ACA YTG RTA C/iBiodT/G GTA C |
| FMDV.TC | 94 | 5'-/5Bio/ACTGGG/iBiodT/TTTACAAAC C/iBiodT/GTGA-3' |
| SVD_1 | 95 | 5'-/5Bio/CAGGA/iBiodT/AATTTCT/iBiodT/CCAAGGGC-3' |
| SVD_2 | 96 | 5'-/5Bio/GACTTG/iBiodT/TGTGGC/iBiodT/GGAGGA-3' |
| SVD_3 | 97 | 5'-/5Bio/GACAAAG/iBiodT/GGCCAAGG GAAA-3' |
| VESV_1 | 98 | 5'-/5Bio/GCCT/iBiodT/CTCCCT/iBiodT/CCCAAAA-3' |
| VESV_3 | 99 | 5'-/5Bio/GGGAA/iBiodT/GAGGTGTGC A/iBiodT/CATT-3' |
| VESV_4 | 100 | 5'-/5Bio/GGTCGC/iBiodT/CTCACTGAT GA/iBiodT/GAGTA-3' |
| VESV_5 | 101 | 5'-/5Bio/ACCACC/iBiodT/CTGGAAACA TC/iBiodT/ATGG-3' |

Covalent Coupling of Oligonucleotide Probes to COOH-Microbeads:

Different sets of carboxylated fluorescent microbeads were obtained from Luminex Corp (Austin, Tex.), and probes for each assay were assigned to a unique bead set. Oligonucleotide probes, with sequences representing the reverse complement to target region of the forward strand (5'-3') were obtained from Integrated DNA Technologies (Coralville, Iowa). Each probe contained a C-18 spacer between the amine reactive group and the 5' end of the oligo to enable optimum hybridization. Probes for each of the pathogen targets were coupled according to the manufacturer recommended coupling protocol. Briefly, a homogenized 1 ml aliquot (1.25×107) of beads was centrifuged for 5 min. at 13,000 rpm, and re-suspended in 50 µl of 100 mM 2-[N-morpholino] ethanesulfonic acid (MES) buffer, pH 4.5. To this suspension, 10 µl of probe at a concentration of 50 µM was added followed by addition of 50 µg of 1-ethyl-3-[3-dimethylaminopropyl]-carbodiimide hydrochloride (EDC) (Pierce Biotechnology [CU1], Rockford, Ill.). This solution was incubated in the dark at room temperature for 30 minutes. A second aliquot of EDC (25 µg) was added and incubated as before. The beads were rinsed in 1 ml phosphate buffered saline (PBS) containing 0.02% Tween-20 (Sigma), centrifuged at 13,000 rpm for 5 min, rinsed using 1 ml of 0.1% (w/v) sodium dodecyl sulfate (SDS) in water, and centrifuged as before. The supernatant was aspirated and the conjugated beads were washed in 100 µl of TE (10 mM Tris, 1 mM EDTA, Ph 8.0 [Sigma]) and then re-suspended in 250 ul TE and stored in the dark at 4° C. Each probe/bead conjugate was stored separately, and a fresh bead set containing all conjugates was prepared for each liquid bead array assay.

Multiplexed PCR Amplification:

Each amplification reaction was performed in a total volume of 25 µl. The reaction mix consisted of 12.5 µl of 2× Superscript III RT-PCR reaction Mix (Invitrogen, Carlsbad, Calif.), 0.1 µl each of forward and reverse primers (each at a concentration of 100 µl), 1 µl per reaction of Superscript III/Platinum Taq Enzyme Mix, 0.95 µl of 50 mM MgSO4 (Invitrogen, Carlsbad, Calif.), 1 µl of 100 copies/µl "Alien RNA" internal control template (Ambion, Austin, Tex.), 5 µl of template, and enough RNase-free water to bring final volume to 25 µl. The "Superscript III RT-PCR System" kit 2× reaction mix contains 0.4 mM of each dNTP and 3.2 mM MgSO4 plus "proprietary stabilizers". With the addition of 0.95 µl of 50 mM MgSO4, the final component concentrations in the 1× reaction mix were as follows: 0.2 mM each dNTP, 3.5 mM MgSO4, 1× Superscript III RT-PCR buffer, 0.4 µM of each primer, and 300 copies of Tobacco Mosaic Virus internal control template. The Platinum Taq polymerase used is a "Hot Start" Taq that is robust and is held by binding a thermolabile inhibitor containing monoclonal antibodies to Taq polymerase.

Thermocycling conditions were as follows: 30 min at 55° C., 2 min at 95° C., followed by 35 cycles of 15 sec at 94° C., 30 sec at 60° C., 15 sec at 72° C., and concluding with one cycle at 72° C. for 2 min. followed by 4° C. soak.

Hybridization of Amplified Sample to the Bead:

A bead set was prepared, consisting of a mixture of 3 µl of beads each covalently coupled to a probe listed in Table 1 into a volume equal to 1 ml of Tris-NaCl buffer (100 mM Tris, 0.05% Triton X100, 200 mM NaCl pH 8.0). Amplified PCR reaction product, e.g., amplicon (1 µl) was added to 22 µl of the bead mix. PCR products and bead mix were denatured at 95° C. for 2 min and allowed to hybridize at 55° C. for 5 min. The mix was transferred to a 96 well filter plate (Millipore, Bedford, Mass.). The beads were washed twice in 100 µl Tris-NaCl and incubated with 60 µl of 3 ng/µl Streptavidin-phycoerythrin (SAPE) (Caltag Laboratories, Burlingame, Calif.) for 5 min. The hybridized beads were washed again with 100 µl Tris-NaCl buffer and re-suspended in a final volume of 100 µl Tris-NaCl buffer. The completed sample was then introduced to the Luminex flow analyzer for analysis.

Example 6

Controls for the Multiplexed Liquid Format Assay

Controls that convey important diagnostic information regarding reagent addition, quality and concentration, assay operator performance, and instrument stability can be easily added without compromising or limiting the screening capabilities of an assay. The disclosed assays employ a unique set of four rationally-designed internal controls built into every sample that monitors and reports every step of the assay.

IC: Instrument Control: The purpose of this control is to inform the user of the reporter laser's integrity and utility. It is a bead coupled to BSA conjugated to tetramethylrhodamine (TAMRA), a heat stable fluorophore; it automatically fluoresces and generates a signal in the presence of the reporter laser. If one notices a decline in the signal, it is due to decline in the laser's integrity. Under those circumstances, one must contact BioRad (or Luminex Customer Support) for a service request. The laser's output is important to monitor because it has a finite lifespan. This control is generally the most robust.

FC: Fluorescence Control/SAPE Addition Control: As a fluorescent control, or SAPE addition control, biotinylated BSA (b-BSA) is coupled to one of the beads. The biotin molecule has a very high binding affinity for streptavidin (biotin-avidin binding) and the Phycoerythrin (PE) component of SAPE is what is detected by the reporter laser (same as the fluorophore bound directly to the bead for the IC). If one does not detect a signal on the FC, then it is likely that SAPE was not added.

NC: Negative Binding Control: The NC is a bead bound to a DNA sequence specific to a random sequence from the genome of an organism found at the bottom of the ocean (Maritima maritensis, Mt7). MT-7 is a conserved DNA sequence from a maritima organism (a thermal vent microbe) that does not match those of published genomes of terrestrial organisms, and serves as a non-specific binding control in the multiplex PCR assay. In the absence of non-specific binding, the MFI values for the NC MT-7 bead should remain consistently low.

PCR/RT-PCR PC: RNA Amplification Control/Inhibition Control: Alien armored RNA (arRNA Alien) is a synthetic RNA sequence, ~1000 nucleotides in length, packaged in an MS2 phage (protein capsid). The sequence is termed "alien" as it has no homology to currently annotated GenBank sequences. Packaging increases the stability of the RNA in clinical sample matrices and more closely mimics the behavior of target virus particles during processing. An internal control assay for alien armored RNA was incorporated into the multiplex PCR assay using specific primers and probe. Alien armored RNA is used as an end-to-end internal control for reverse transcription, PCR amplification, Luminex microsphere array hybridization and Bio-Plex detection.

The alien RNA concentration used is typically 200 copies per well, which consistently yields a median fluorescent intensity (MFI) value above the assay detection limit for both clean and clinical sample matrixes. A low number copy number for the internal control was selected to minimize competition within the PCR reaction with the agent signatures. A low copy number can also better reflect detrimental changes in assay performance that could potentially result in a false negative. MFI values below threshold may indicate failed reverse transcription and PCR amplification, or a failed hybridization reaction.

The controls used in the multiplexed liquid format assay are shown in the following table.

TABLE 7

Controls for multiplexed liquid format assay

| Control | Description | Sequence (5' => 3') | SEQ ID NO | Organism |
|---|---|---|---|---|
| Instrument Control | Luminex probe | 5'-/5AmMC6//iSp18/CAAAGTGGGAGACGTCGTTG-3'Cy3 | 102 | Maritima 7-Cy3 |
| Fluorescence Control | Luminex probe | 5'-/5AmMC6//iSp18/CAAAG/iBiodT/GGGAGACGTCG/iBiodT/TG-3' | 103 | Maritima 7- biotin |
| Negative Control | Luminex probe | 5'-/5AmMC6//iSp18/CAAAGTGGGAGACGTCGTTG-3' | 104 | Maritima 7 |
| PCR Amplification/ Inhibition Control | Forward primer | 5'GACATCAAGGCTCAAACTAATTTTACC 3' | 105 | n/a |
| PCR Amplification/ Inhibition Control | Reverse primer | 5'CAAAGGCTGCCAACATAAAATG 3' | 106 | n/a |
| PCR Amplification/ Inhibition Control | Luminex probe | 5'-/5AmMC6//iSp18/CAAGCGTAAATGCAGCGTCCA-3' | 107 | n/a |

The controls are used to verify the integrity of the assay. Control results are used to determine whether the results for a given sample are valid or not. Assay integrity is determined using the following processes:

First, for each sample, MFI values for the 4 control bead classes are checked against a corresponding threshold. The thresholds used for the panel are still being determined and cannot be established until the multiplexed assay panel development is complete (i.e., no additional signatures are added). In general, if MFI values for the IC, NC or FC controls are out of range then the results from that sample are deemed invalid and excluded from further analysis.

Second, if the MFI value of the alien armored RNA control is out of range AND none of the MFI values for the 17 agent channels exceed threshold, then the results from that sample are deemed invalid and excluded from further analysis. If the MFI for the alien armored RNA control is out of range AND one or more of the MFI values for the 17 agent channels exceeds threshold, then the results from that sample are deemed valid and included in further analysis. We have observed that agent spikes above certain concentrations can cause a decrease in the alien armored RNA MFI, probably due to competition in the PCR reaction. When the alien armored RNA MFI drops below threshold on a sample considered negative for all signatures, the analysis would be discarded and would need to be repeated. This control reduces the probability of false negatives.

Third, if the MFI values for all four controls are within range, bead counts are checked. First, the bead counts for each of the 4 controls are checked. If the bead count minimum (40 beads) for any of the 4 controls was not reached, then the control MFI values are deemed invalid, and all assay results for that sample are excluded from further analysis.

The final step is to check the individual bead count for each of the 17 signatures for a given sample (non-control beads). If an individual agent bead class (signature) does not reach the bead count minimum (40 beads), that individual assay result is deemed invalid and only that individual result for that signature is removed from the analysis. If the bead counts for any of the agent channels exceeded the minimum, they are considered valid and included in the analysis.

Figure 4:
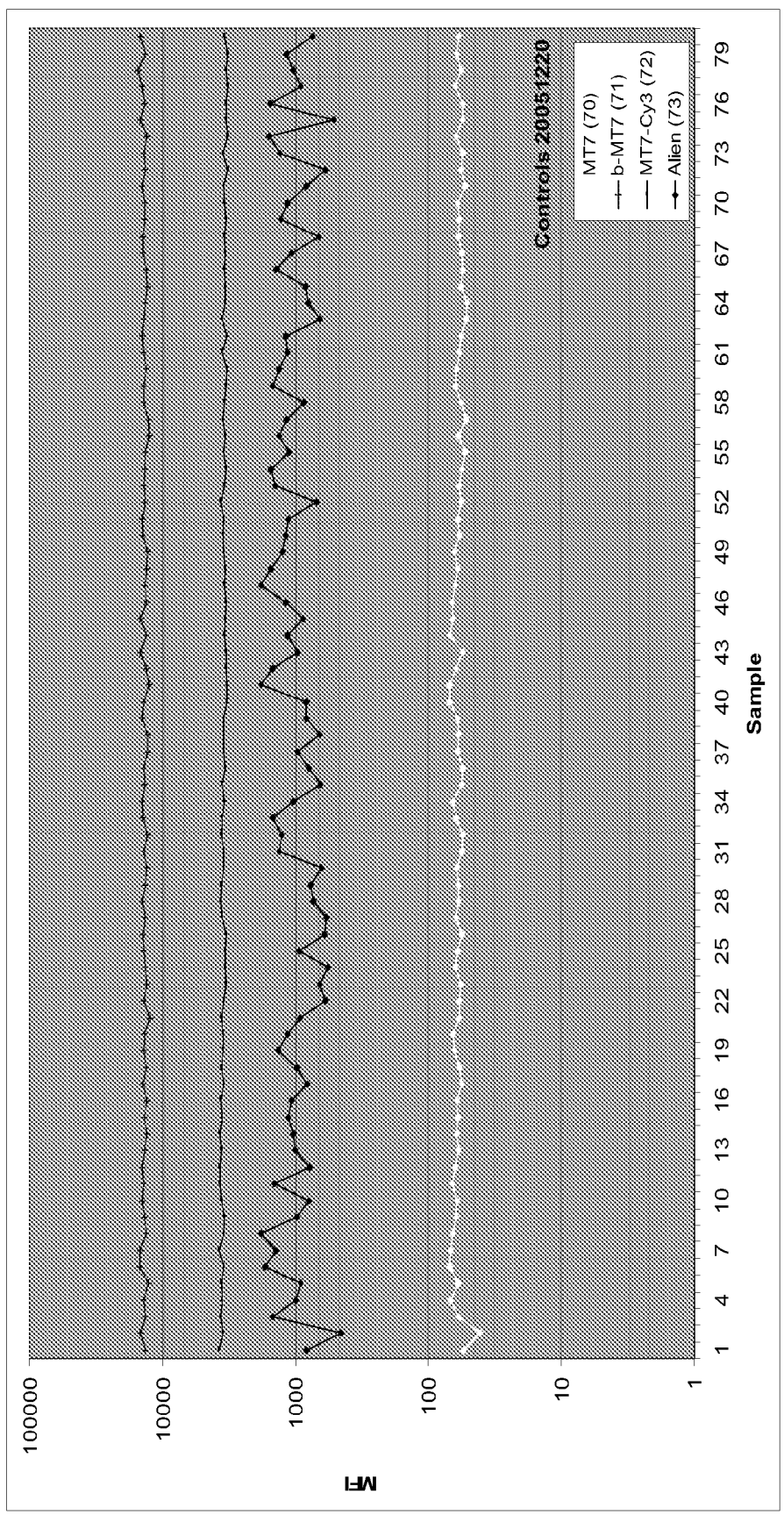
FIG. 4 a typical plot showing the MFI of four controls recorded in a multiplexed assay PCR assay across a microtiter plate (96-wells, 80 samples tested) and analyzed using a Luminex detector. The log of the median fluorescence intensity (MFI) is plotted on the Y-axis versus sample number shown on the X-axis. Each sample contains 4 internal controls. Controls should produce data that is constant form one sample to the next; therefore data in plots like this one should exhibit 4 straight lines. Fluctuations in MFI values for any of the 4 controls can indicate a problem with the assay. Additionally, each control is characterized by its inherent variation. Some controls produce data that is much less variable than others. The high deviation from point to point shown on this plot from the positive control Alien RNA is expected and normal.

A flow diagram of the process used to determine whether or not any individual assay result is valid or not is shown in FIG. 4.

Example 7

Limits of Detection

The panel of selected signature sequences was tested for the limit of detection (LOD) in both the single plex and multiplex format. The results are presented below.

TABLE 8

Limits of Detection (LOD)

| Assay ID | Target DNA | Reference Test Strain | Singleplex LOD | Multiplex LOD | LOD shift (logs) | Bkgrd SP | Bkgd Mux | Threshold (MFI) | Cross-reactivities with panel constituents |
|---|---|---|---|---|---|---|---|---|---|
| BVH_1 | Bovine Herpes | BHV_N/A | 100 viral particles/ | 100 viral | 0 | 9 | 60 | 120 | None Noted |

TABLE 8-continued

Limits of Detection (LOD)

| Assay ID | Target DNA | Reference Test Strain | Singleplex LOD | Multiplex LOD | LOD shift (logs) | Bkgrd SP | Bkgd Mux | Threshold (MFI) | Cross-reactivities with panel constituents |
|---|---|---|---|---|---|---|---|---|---|
| | Virus | | uL | particles/uL | | | | | |
| BVH_3 | Bovine Herpes Virus | BHV_N/A | 100 viral particles/uL | 100 viral particles/uL | 0 | 10 | 40 | 980 | None Noted |
| BPSV_1 | Bovine Papular Stomatitis Virus | BPSV_N/A | 1000 viral particles/uL | 100 viral particles/uL | −1 | 10 | 30 | 125 | None Noted |
| BPSV_2 | Bovine Papular Stomatitis Virus | BPSV_N/A | 10 viral particles/uL | 10 viral particles/uL | 0 | 10 | 65 | 140 | Background cross-reactivity, not well defined |
| BPSV_4 | Bovine Papular Stomatitis Virus | BPSV_N/A | 100 viral particles/uL | 100 viral particles/uL | 0 | 10 | 35 | 600 | None Noted |
| FMDV.TC | Foot and Mouth Virus | 01 Manisa | $1 \times 10^{-8}$ pfu/ul | $1 \times 10^{-6}$ pfu/ul | 2 | 10 | 10 | 150 | None Noted |
| FMDV.Pir | Foot and Mouth Virus | 01 Manisa | $1 \times 10^{-4}$ pfu/ul | $1 \times 10^{-4}$ pfu/ul | 0 | 10 | 10 | 200 | None Noted |
| BVD_1a | Bovine Viral Diarrhea | BVD_N/A | 10 viral particles/uL | 10 viral particles/uL | 0 | 7 | 30 | 110 | None Noted |
| BTV_2 | Bluetongue Virus | BTV-13 | 1 viral particles/uL | 1 viral particles/uL | 0 | 11 | 30 | 90 | None Noted |
| BTV_3 | Bluetongue Virus | BTV-13 | 1 viral particles/uL | 10 viral particles/uL | 1 | 9 | 20 | 1000 | None Noted |
| SVD_1 | Swine Vesicular Disease | ITL/1/66 | $1 \times 10^{-6}$ pfu/ul | $1 \times 10^{-5}$ pfu/ul | 1 | 5 | 8 | 135 | None Noted |
| SVD_2 | Swine Vesicular Disease | ITL/1/66 | $1 \times 10^{-6}$ pfu/ul | $1 \times 10^{-4}$ pfu/ul | 2 | 10 | 10 | 150 | None Noted |
| SVD_3 | Swine Vesicular Disease | ITL/1/66 | $1 \times 10^{-5}$ pfu/ul | $1 \times 10^{-5}$ pfu/ul | 0 | 16 | 16 | 200 | None Noted |
| VESV_1 | Vesicular Exanthema of Swine Virus | E54[1]/A48[2] | $1 \times 10^{-6}$ pfu/ul | $1 \times 10^{-3}$ pfu/ul | N/A | 5 | 5 | 80 | None Noted |
| VESV_3 | Vesicular Exanthema of Swine Virus | A48[1]/A48[2] | $1 \times 10^{-6}$ pfu/ul | $1 \times 10^{-6}$ pfu/ul | N/A | 22 | 18 | 500 | None Noted |
| VESV_4 | Vesicular Exanthema of Swine Virus | E54[1]/A48[2] | $1 \times 10^{-6}$ pfu/ul | $1 \times 10^{-5}$ pfu/ul | N/A | 25 | 17 | 700 | None Noted |
| VESV_5 | Vesicular Exanthema of Swine Virus | A48[1]/A48[2] | $1 \times 10^{-6}$ pfu/ul | $1 \times 10^{-6}$ pfu/ul | N/A | 23 | 20 | 100 | None Noted |

Example 8

Disease Signature Thresholds

Thresholds were initially determined using all available data from known negative samples (blanks) by plotting a histogram that showed the probability of a given sample generating a particular MFI. In the absence of cross reactivity, each signature in the multiplex assay could be treated as an individual assay result. For example, for a sample spiked with BPSV virus, data for other disease signatures could contribute towards negative data, providing that cross reaction between disease signature sets was not observed. This is a way to increase the number of samples that can be used to establish thresholds.

To determine the degree of cross reactivity for each assay, the probability of obtaining a given MFI was plotted versus MFI for both true blank samples and spiked samples. Signatures intended to detect a virus-spiked sample were excluded from this analysis. Histograms generated from virus positive samples and true blank samples were not significantly different; the distributions indicated negligible cross reactivity. Using all negative sample data, a receiver operator characteristic (ROC) function describing the relationship between threshold values and the rate at which false positives occur was plotted. The threshold was determined from the ROC function by finding the MFI values that would yield a false positive at a given rate. A false positive rate of 0.002 was selected, which corresponds to 1 false positive every 500 samples. The resolution in false positive rate is determined by the number of samples that are present. For example to establish a false positive rate of 0.0001, or 1 false positive per 10,000 samples, a minimum of 10,000 samples are required.

The threshold values that were established for the assay controls and each signature in the multiplex assay panel are shown below. The BPSV-2 threshold was set at 400. The MFI value for a false positive rate of 0.002 was 730. This resulted in a sensitivity which was too low for the samples virus concentrations used.

TABLE 9

Threshold values for signature sequences

| Signature | Threshold (MFI) |
|---|---|
| BHV-1 | >49 |
| BHV-3 | >43 |
| BPSV-1 | >35 |
| BPSV-2* | >400 |
| BPSV-4 | >41 |
| FMDV-1 | >42 |
| FMDV-2 | >60 |
| BVD-1a | >40 |
| BTV-2 | >55 |
| BTV-3 | >31 |
| SVD-1 | >38 |
| SVD-2 | >28 |
| SVD-3 | >40 |
| VESV-1 | >24 |
| VESV-3 | >39 |
| VESV-4 | >105 |
| VESV-5 | >56 |

Example 9

Data from Multiplexed Luminex Assay

Figure 5A:
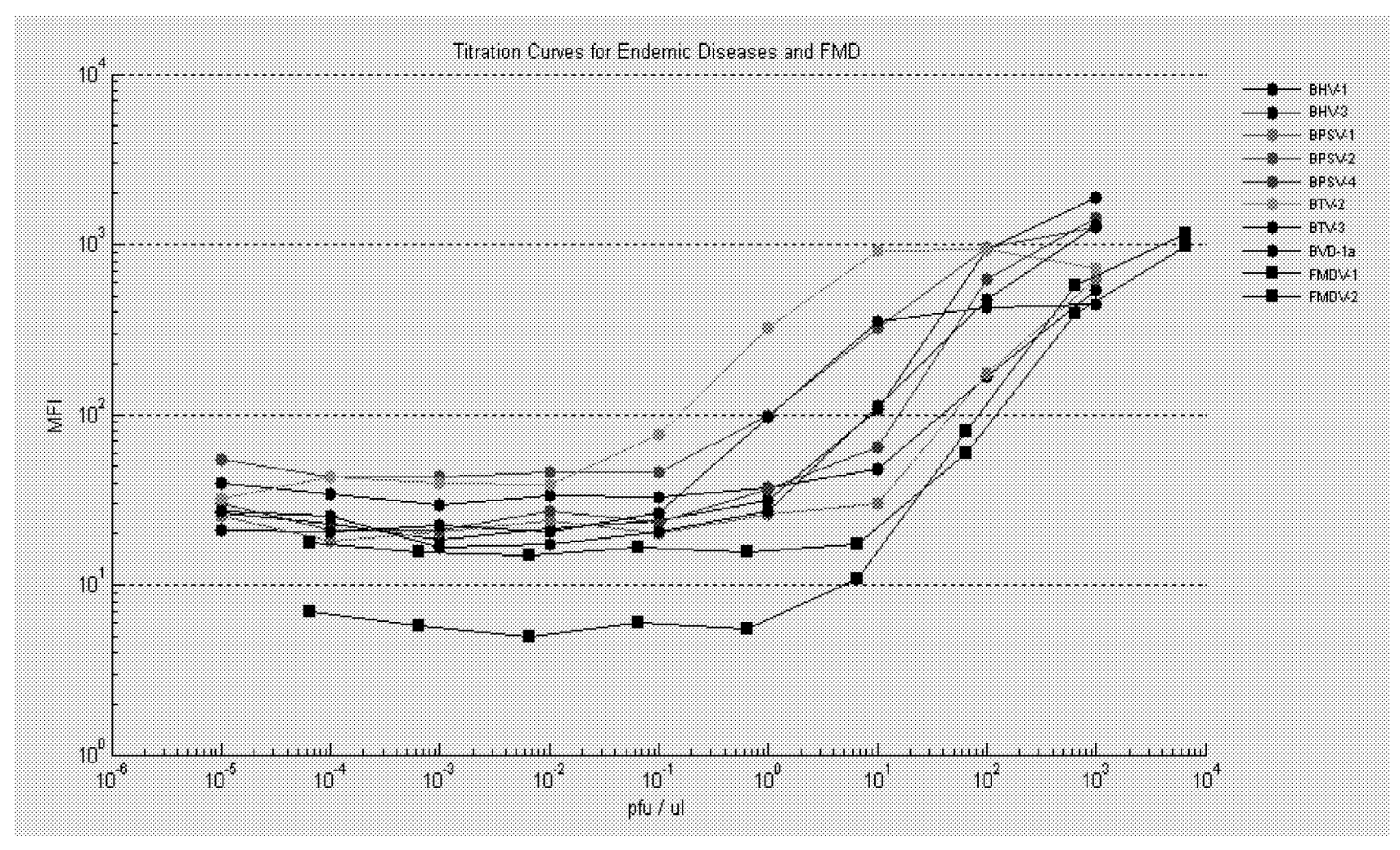
Figure 5B:
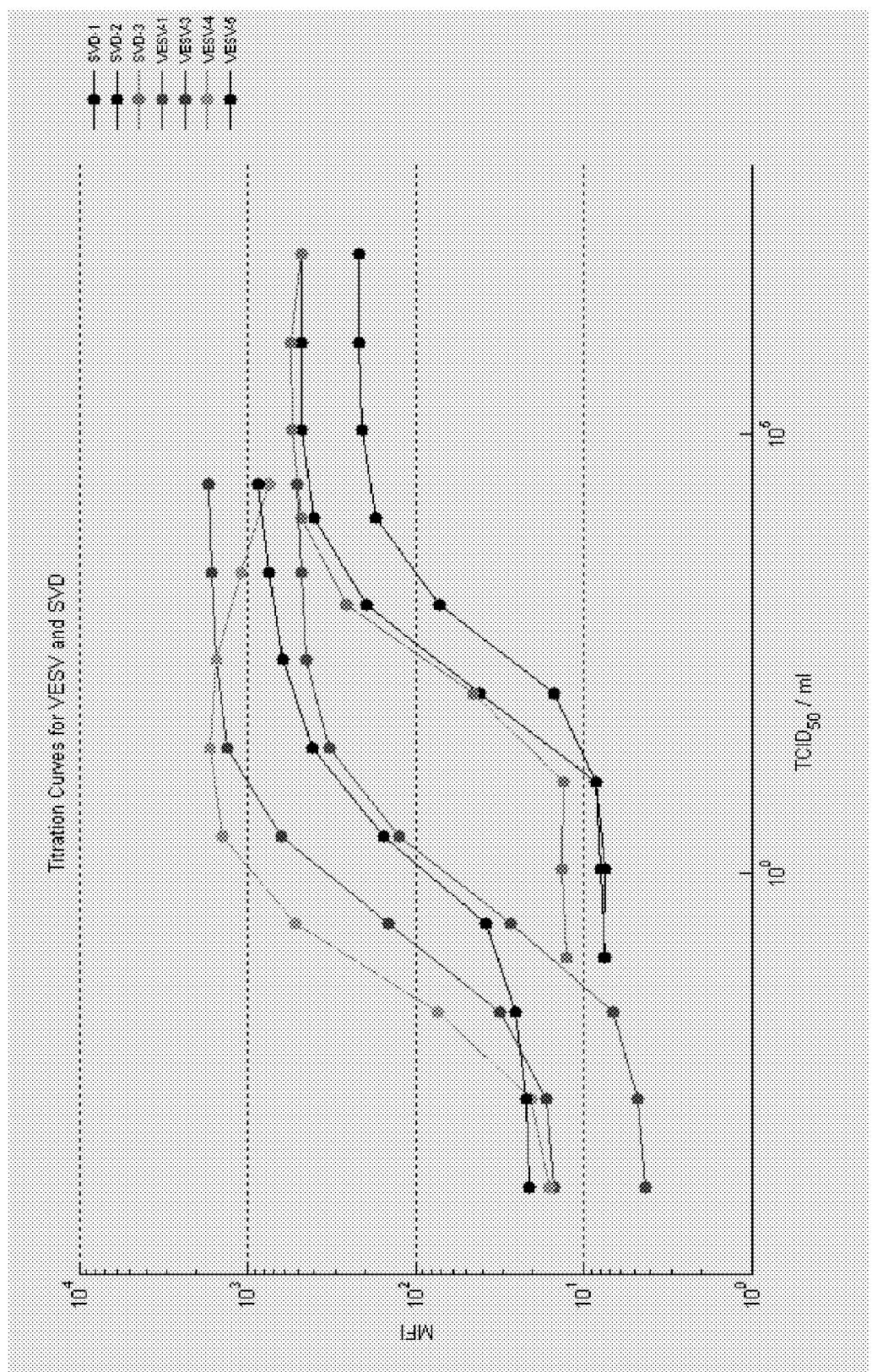
FIG. 5B: The curves combined herewith represent common viral extraction units (TCID50/mL) of representative strains for SVD and VESV.

FIG. 5 is plot of dose-response curves for select domestic and foreign animal diseases that constitute the FMDV rule-out panel as described in Table 1. The curves combined herewith represent common viral extraction units (pfu/mL) of representative strains for BHV, BPSV, BTV, BVDV and FMDV. The results demonstrate that the signature sequences described in Table 1 effectively detect and differentiate between multiple pathogens in a sample.

Example 10

Multiplexed Detection of Agricultural Pathogens Using a Microarray Approach

In another embodiment, the signature sequences used herein are used for detection of pathogens in a sample using a microarray, e.g., a microarray manufactured by Nimblegen Systems. Nimblegen builds its arrays based on photodeprotection chemistry using its proprietary Maskless Array Synthesizer (MAS) system. The Digital Micromirror Device, at the heart of the system, creates digital masks whose design can be easily changed. Up to 390,000 custom oligos can be synthesized onto glass slides within a few hours. To detect the agricultural pathogens, oligonucleotide probes of up to 70 bases long that are complementary to the signature sequences disclosed herein are designed using a set of probe design parameters. Due to the ultra high density, multiple probes from the same sequence can be included on the same chip with on-chip replicates, which increases the confidence in probe calls. A variety of techniques for probe design can be employed, ranging from non-overlapping (sampling) to overlapping (tiling) to the detection of Single Nucleotide Polymorphisms (resequencing, using short oligos.) The pathogen nucleic acid sample is amplified with fluorescently labeled random primers and the labeled DNA is hybridized to the chip. The chip is washed to get rid of non-specifically bound samples and scanned using a laser scanner at high resolution. The raw data and images are analyzed using statistical tools and presence/absence calls are made. Though not as sensitive as Taqman assays and bead assays, microarray allows the detection of presence or absence of multiple viruses simultaneously, and shortens the optimization time for multiplexing assays.

Example 11

Additional FMDV Signature Sequences

Using the in-silico identification techniques described herein, additional signature sequences for determining the presence or absence of FMDV in sample were determined as follows.

TABLE 10

Additional FMDV signature sequences

| SEQ ID NO: | Assay reference | SEQUENCE DESCRIPTION | SEQUENCE (5' -> 3') |
|---|---|---|---|
| 108 | FMDV-1261 | Signature sequence | CAAACCTGTGATGGCTTCGAAG ACCCTCGAAGCTATCCTCTCCT TTGCACGCCGTGGGACCATTCA GGAGAAGTTGATCTNNNNNNNN |

TABLE 10-continued

Additional FMDV signature sequences

| SEQ ID NO: | Assay reference | SEQUENCE DESCRIPTION | SEQUENCE (5' -> 3') |
|---|---|---|---|
| | | | NNNNNNNNNNNTCCACTCCGGAC AAGACGAGTACCGGCGTCTCT |
| 109 | FMDV-1261 | Forward primer | CAAACCTGTGATGGCTTCGA |
| 110 | FMDV-1261 | Reverse primer | AGAGACGCCGGTACTCGTCTT |
| 111 | FMDV-1261 | Probe | TGCACGCCGTGGGACCATTC |
| 112 | FMDV-1261R | Signature sequence | AGAGACGCCGGTACTCGTCTTG TCCGGAGTGGANNNNNNNNNNN NNNNNNNAGATCAACTTCTCCT GAATGGTCCCACGGCGTGCAAA GGAGAGGATAGCTTCGAGGGTC TTCGAAGCCATCACAGGTTTG |
| 113 | FMDV-1261R | Forward primer | AGAGACGCCGGTACTCGTCTT |
| 114 | FMDV-1261R | Reverse primer | CAAACCTGTGATGGCTTCGA |
| 115 | FMDV-1261R | Probe | TCCTGAATGGTCCCACGGCGT |
| 116 | FMDV-1674 | Signature sequence | CCAACGCAGGTAAAGTGATCTG TAGCTTGGAATCTCGAACGTCC NNNNNNNNNNNNNNNNNNGAC GCCGGTACTCGTCTTGTCCGGA GTGGANNNNNNNNNNNNNNNN NAGATCAACTTCTCCTGAATGG TCCCACGGCGTGCAAAGGAGAG GATAGCTTCGAGG |
| 117 | FMDV-1674 | Forward primer | CCAACGCAGGTAAAGTGATCTG |
| 118 | FMDV-1674 | Reverse primer | AACCTGTGATGGCTTCGAAGAC |
| 119 | FMDV-1674 | Probe | TCCTGAATGGTCCCACGGCGT |
| 120 | FMDV-3238 | Signature sequence | AGCATCATCAACACAATTCTGA ACAACATCTACGTGCTCTACGC GCTGCGTAGGCACTACGAGGGA GTTGAGCTGGACACTTACACCA TGATCTCCTACGGGGACGACAT CGTGGTTGCAAGTGATTACGAT CTNNNNNNNNNNNNNNNNNNN NNNNNNNNNNNNNNNNNNNNN NNNNNNNNNNNNNNNNNNNNN NNNNNNNNNNNNNNNNNNNNN NNGTCACTCCATTACCGATGTC ACTTTCCTCAAAAGACACTTCC ACATGGATTATGGAACTGGGTT TTACAAACCTGTGATGGCTTCG AAGACCCTCGAAGCCATCCTCT CCTTTGCACGCCGTG |
| 121 | FMDV-3238 | Forward primer | AGCATCATCAACACAATTCTGA ACA |
| 122 | FMDV-3238 | Reverse primer | CATCACAGGTTTGTAAAACCCA GTT |
| 123 | FMDV-3238 | Probe | CACTTTCCTCAAAAGACACTTC CACATGGATTATG |

The signature sequences disclosed in Table 9 are used, either individually or in combination with each other, in kits and methods disclosed herein for determining the presence or absence of FMDV in a sample by detection of the signature sequences. The kits and methods use the signature sequences disclosed in Table 9 alone or in combination with one or more additional signature sequences from FMDV and other agricultural pathogens, e.g., those disclosed in Table 1.

For detection of the signature sequences via amplification, primers suitable for PCR were designed and are disclosed in Table 9. The forward and reverse primers in Table 9 are used for PCR based detection of FMDV in a sample via detection of the signature sequences disclosed in Table 9 in the sample. Detection of the amplicon, e.g., the amplified signature sequence, is performed using an agarose gel.

For detection of signature sequences using real-time PCR, probes suitable for Taqman PCR were designed and are disclosed in Table 9. The primers and probes in Table 9 are used for Taqman PCR based detection of FMDV in a sample via detection of the signature sequences disclosed in Table 9 in a sample. Detection of the amplicon, e.g., the amplified signature sequence, is performed using an iCycler.

The primers and probes are also used for Luminex based detection of the signature sequences in Table 9. Probes are covalently attached to fluorescent microbeads and hybridized to samples subjected to PCR using the disclosed primers.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A kit for determining the presence or absence of at least two pathogens in a sample, said pathogens selected from the group consisting of Bovine Herpes Virus (BVH), Bovine Papular Stomatitus Virus (BPSV), Bovine Viral Diarrhea (BVD), Blue Tongue Virus (BTV), Swine Vesicular Disease Virus (SVD), and Vesicular Exanthema of Swine Virus (VESV), said kit comprising nucleic acid reagents for detection of a first nucleic acid signature sequence consisting of SEQ ID NO:1 for detection of Bovine Herpes Virus (BVH) and nucleic acid reagents for detection of a second nucleic acid signature sequence consisting of SEQ ID NO:9 for detection of Bovine Papular Stomatitus Virus (BPSV).

2. The kit of claim 1, said kit further comprising nucleic acid reagents for detection of at least one additional nucleic acid signature sequence selected from the group consisting of: for pathogen BVH, signature sequence consisting of SEQ ID NO:5; for pathogen BPSV, signature sequences consisting of SEQ ID NO:13 and SEQ ID NO:17; for pathogen BVD, signature sequences consisting of SEQ ID NO:29; for pathogen BTV, signature sequences consisting of SEQ ID NO:33 and SEQ ID NO:37; for pathogen SVD, signature sequences consisting of SEQ ID NO:41 and SEQ ID NO:45 or SEQ ID NO:49; and for pathogen VESV, signature sequences consisting of SEQ ID NO:53 and SEQ ID NO:57 and SEQ ID NO:61 and SEQ ID NO: 65.

3. The kit of claim 1 or claim 2, further comprising reagents for determining the presence or absence of Foot and Mouth Disease Virus (FMDV) in the sample, said kit further comprising nucleic acid reagents for detection of at least one nucleic acid signature sequence selected from the group consisting of SEQ ID NO:21 and SEQ ID NO:25.

4. The kit of claim 1 for determining the presence or absence of BVH, BPSV, FMDV; BVD, BTV; SVD; and VESV in a sample, said kit comprising nucleic acid reagents for detection of nucleic acid signature sequences consisting of SEQ ID NO:1, SEQ ID NO:5, SEQ ID NO:9, SEQ ID NO:13, SEQ ID NO:17, SEQ ID NO:21, SEQ ID NO:25, SEQ ID NO:29, SEQ ID NO:33, SEQ ID NO:37, SEQ ID NO:41, SEQ ID NO:45, SEQ ID NO:49, SEQ ID NO:53, SEQ ID NO:57, SEQ ID NO:61, and SEQ ID NO: 65.

5. The kit of claim 1 or 4, wherein said reagents comprise a set of oligonucleotides for each signature sequence to be detected, said set comprising PCR primers and hybridization probes for each signature sequence.

6. The kit of claim 1, wherein said reagents comprise PCR primers and hybridization probes, wherein the PCR primers consist of SEQ ID NO:2 and SEQ ID NO:3 and SEQ ID NO:10 and SEQ ID NO:11, and the hybridization probes consist of SEQ ID NO:4 and SEQ ID NO:12.

7. The kit of claim 4, wherein said reagents comprise PCR primers and hybridization probes consisting of SEQ ID NO:2, SEQ ID NO:3, SEQ ID NO:6, SEQ ID NO:7, SEQ ID NO:10, SEQ ID NO:11, SEQ ID NO:14, SEQ ID NO:15, SEQ ID NO:18, SEQ ID NO:19, SEQ ID NO:22, SEQ ID NO:23, SEQ ID NO: 26, SEQ ID NO:27, SEQ ID NO:30, SEQ ID NO:31, SEQ ID NO:34, SEQ ID NO:35, SEQ ID NO:38, SEQ ID NO:39, SEQ ID NO:42, SEQ ID NO:43, SEQ ID NO:46, SEQ ID NO:47, SEQ ID NO:50, SEQ ID NO:51, SEQ ID NO:54, SEQ ID NO:55, SEQ ID NO:58, SEQ ID NO:59, SEQ ID NO:62, SEQ ID NO:63, SEQ ID NO:66, SEQ ID NO:67, SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO: 60, SEQ ID NO:64, and SEQ ID NO:68.

8. The kit of claim 7, further comprising reagents for detection of control sequences, wherein the reagents comprise of SEQ ID NO: 85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, and SEQ ID NO:101.

9. The kit of claim 5, wherein said hybridization probes are affixed to a bead.

10. A method for determining the presence or absence of at least two pathogens selected from the group consisting of BVH, BPSV, BVD, BTV; SVD; and VESV in a sample, said method comprising the steps of using the kit of claim 1.

11. A method for determining the presence or absence of at least two pathogens selected from the group consisting of BVH, BPSV, BVD, BTV; SVD; and VESV in a sample, said method comprising the steps of using the kit of claim 3.

12. The method of claim 10, wherein said method includes a PCR amplification of each signature sequence.

13. A method for determining the presence or absence of BVH, BPSV, FMDV; BVD, BTV; SVD, and VESV in a sample, said method comprising the steps of using the kit of claim 4.

14. The method of claim 13, wherein said method includes PCR amplification of each signature sequence.

15. A method for determining the presence or absence of BVH, BPSV, FMDV; BVD, BTV; SVD, and VESV in a sample, said method comprising the steps of using the kit of claim 7.

16. The kit of claim 1, said kit further comprising nucleic acid reagents for detection of at least one additional nucleic acid signature sequence, wherein the additional nucleic acid signature sequence is selected from the group consisting of: for pathogen BVD, signature sequences consisting of SEQ ID NO:29; for pathogen BTV, signature sequences consisting of SEQ ID NO:33 and SEQ ID NO:37; for pathogen SVD, signature sequences consisting of SEQ ID NO:41 and SEQ ID NO:45 and SEQ ID NO:49; and for pathogen VESV, signature sequences consisting of SEQ ID NO:53 and SEQ ID NO:57 and SEQ ID NO:61 and SEQ ID NO: 65.

17. The kit of claim 2, wherein said reagents comprise PCR primers and hybridization probes, wherein the PCR primers are selected from the PCR primers of SEQ ID NO:14 and SEQ ID NO:15, the PCR primers of SEQ ID NO:18 and SEQ ID NO:19, the PCR primers of SEQ ID NO:30 and SEQ ID NO:31, the PCR primers of SEQ ID NO:34 and SEQ ID NO:35, the PCR primers of SEQ ID NO:38 and SEQ ID NO:39, the PCR primers of SEQ ID NO:42 and SEQ ID NO:43, the PCR primers of SEQ ID NO:46 and SEQ ID NO:47, the PCR primers of SEQ ID NO:50 and SEQ ID NO:51, the PCR primers of SEQ ID NO:54 and SEQ ID NO:55, the PCR primers of SEQ ID NO:58 and SEQ ID NO:59, the PCR primers of SEQ ID NO:62 and SEQ ID NO:63, the PCR primers of SEQ ID NO:66 and SEQ ID NO:67, and wherein the hybridization probes comprise SEQ ID NO:8, SEQ ID NO:16, SEQ ID NO:20, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64 and SEQ ID NO:68.

* * * * *